United States Patent
Borden et al.

(10) Patent No.: US 7,379,185 B2
(45) Date of Patent: May 27, 2008

(54) EVALUATION OF OPENINGS IN A DIELECTRIC LAYER

(75) Inventors: Peter G. Borden, San Mateo, CA (US); Jiping Li, Fremont, CA (US); Edgar Genio, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 359 days.

(21) Appl. No.: 10/979,397

(22) Filed: Nov. 1, 2004

(65) Prior Publication Data

US 2006/0094136 A1    May 4, 2006

(51) Int. Cl.
*G01N 21/55* (2006.01)
(52) U.S. Cl. ............... 356/445; 356/635; 356/237.1
(58) Field of Classification Search ............ 356/626, 356/432, 445–448, 237.1, 237.5, 237.6
See application file for complete search history.

(56) References Cited

U.S. PATENT DOCUMENTS

| | | | |
|---|---|---|---|
| 3,462,602 A | 8/1967 | Apple | 250/83 |
| 3,909,602 A | 9/1975 | Micka | 716/4 |
| 4,255,971 A | 3/1981 | Rosencwaig | 73/606 |
| 4,468,136 A | 8/1984 | Murphy et al. | 374/45 |
| 4,513,384 A | 4/1985 | Rosencwaig | 702/170 |
| 4,521,118 A | 6/1985 | Rosencwaig | 374/5 |
| 4,522,510 A | 6/1985 | Rosencwaig | 374/7 |
| 4,560,273 A * | 12/1985 | Ando et al. | 356/237.6 |
| 4,579,463 A | 4/1986 | Rosencwaig et al. | 374/57 |
| 4,632,561 A | 12/1986 | Rosencwaig et al. | 356/432 |
| 4,634,290 A | 1/1987 | Rosencwaig | 374/5 |
| 4,636,088 A | 1/1987 | Rosencwaig et al. | 374/5 |

(Continued)

FOREIGN PATENT DOCUMENTS

EP    0 718 595    12/1995

(Continued)

OTHER PUBLICATIONS

D. K. Schroder, "Semiconductor Material and Device Characterization", 2nd Edition, A Wiley-Interscience Publication, John Wiley & Sons Inc. (month unavailable), 1998, pp. 587-594, 603-609.

(Continued)

*Primary Examiner*—Layla G. Lauchman
*Assistant Examiner*—Juan D Valentin, II
(74) *Attorney, Agent, or Firm*—Omkar Suryadevara

(57) ABSTRACT

A patterned dielectric layer is evaluated by measuring reflectance of a region which has openings. A heating beam may be chosen for having reflectance from an underlying conductive layer that is several times greater than absorptance, to provide a heightened sensitivity to presence of residue and/or changes in dimension of the openings. Reflectance may be measured by illuminating the region with a heating beam modulated at a preset frequency, and measuring power of a probe beam that reflects from the region at the preset frequency. Openings of many embodiments have sub-wavelength dimensions (i.e. smaller than the wavelength of the heating beam). The underlying conductive layer may be patterned into links of length smaller than the diameter of heating beam, so that the links float to a temperature higher than a corresponding temperature attained by a continuous trace that transfers heat away from the illuminated region by conduction.

48 Claims, 16 Drawing Sheets

U.S. PATENT DOCUMENTS

| | | | |
|---|---|---|---|
| 4,679,946 A | 7/1987 | Rosencwaig et al. | 374/5 |
| 4,750,822 A | 6/1988 | Rosencwaig et al. | 324/445 |
| 4,795,260 A | 1/1989 | Schuur et al. | 356/400 |
| 4,950,990 A | 8/1990 | Moulder | 324/224 |
| 5,074,669 A | 12/1991 | Opsal | 356/447 |
| 5,087,121 A * | 2/1992 | Kakuchi et al. | 356/626 |
| 5,149,978 A | 9/1992 | Opsal et al. | 250/234 |
| 5,159,412 A | 10/1992 | Willenborg et al. | 356/445 |
| 5,181,080 A | 1/1993 | Fanton et al. | 356/381 |
| 5,228,776 A | 7/1993 | Smith et al. | 374/5 |
| 5,229,304 A | 7/1993 | Chang et al. | 437/7 |
| 5,377,006 A | 12/1994 | Nakata | 356/349 |
| 5,379,109 A | 1/1995 | Gaskill et al. | 356/445 |
| 5,574,562 A | 11/1996 | Fishman et al. | 356/432 |
| 5,610,710 A * | 3/1997 | Canfield et al. | 356/237.6 |
| 5,706,094 A | 1/1998 | Maris | 356/432 |
| 5,798,529 A | 8/1998 | Wagner | 250/492 |
| 5,877,860 A | 3/1999 | Borden | 356/376 |
| 5,883,518 A | 3/1999 | Borden | 324/752 |
| 5,903,343 A * | 5/1999 | Ning et al. | 356/237.1 |
| 5,966,019 A | 10/1999 | Borden | 324/752 |
| 5,978,074 A | 11/1999 | Opsal et al. | 356/72 |
| 6,040,936 A | 3/2000 | Kim et al. | 356/245 |
| 6,049,220 A | 4/2000 | Borden et al. | 324/765 |
| 6,054,868 A | 4/2000 | Borden et al. | 324/752 |
| 6,154,280 A | 11/2000 | Borden | 356/376 |
| 6,268,916 B1 | 7/2001 | Lee et al. | 356/432 |
| 6,281,027 B1 | 8/2001 | Wei et al. | 438/14 |
| 6,323,951 B1 | 11/2001 | Borden et al. | 356/502 |
| 6,426,644 B1 | 11/2001 | Borden et al. | 324/765 |
| 6,327,035 B1 | 12/2001 | Li et al. | 356/432 |
| 6,395,563 B1 | 5/2002 | Eriguchi | 438/7 |
| 6,411,389 B1 | 6/2002 | Rushford | 356/492 |
| 6,483,594 B2 | 11/2002 | Borden et al. | 356/502 |
| 6,486,965 B1 | 11/2002 | Kim | 356/626 |
| 6,489,624 B1 | 12/2002 | Ushio et al. | 250/559 |
| 6,489,801 B1 | 12/2002 | Borden et al. | 324/766 |
| 6,528,333 B1 | 3/2003 | Jun et al. | 438/16 |
| 6,694,284 B1 | 2/2004 | Nikoonahad et al. | 702/155 |
| 6,720,248 B2 | 4/2004 | Ryo | 438/622 |
| 6,734,968 B1 | 5/2004 | Wang et al. | 356/369 |
| 6,747,355 B2 | 6/2004 | Abiru et al. | 257/758 |
| 6,804,003 B1 | 10/2004 | Wang et al. | 356/369 |
| 6,812,047 B1 | 11/2004 | Borden et al. | 438/16 |
| 7,009,695 B2 * | 3/2006 | Some | 356/237.1 |
| 7,061,599 B2 * | 6/2006 | Yokochi et al. | 356/237.1 |
| 2001/0028454 A1 * | 10/2001 | Savareigo | 356/237.5 |
| 2002/0027654 A1 * | 3/2002 | Owen et al. | 356/237.5 |
| 2002/0126732 A1 | 9/2002 | Shakouri et al. | 374/130 |
| 2002/0167326 A1 | 11/2002 | Borden et al. | 324/765 |
| 2003/0155927 A1 | 8/2003 | Pinto et al. | 324/501 |
| 2004/0218180 A1 | 11/2004 | Rosencwaig et al. | 356/369 |

FOREIGN PATENT DOCUMENTS

| | | |
|---|---|---|
| JP | 2000 009443 A | 1/2000 |
| WO ISR PCT/US99/12999 | | 6/1999 |
| WO ISR PCT/US01/07475 | | 7/2001 |
| WO ISR PCT/US03/02650 | | 2/2003 |
| WO ISR PCT/US03/06239 | | 2/2003 |
| WO ISR PCT/US03/06379 | | 2/2003 |

OTHER PUBLICATIONS

J.M. Ziman, F.R.S., "Principles of the Theory of Solids", 2nd Edition, Cambridge At the University Press 1972, pp. 278-282.

"Residue Removers ST-250", The Industry Standard for Removing Plasma Etch Residues, ©2001 ATMI, Inc. pp. 2.

A. Krishnamoorthy, V. Bliznetsov, H. Leng Yay and B. Yo, "Effect of Etching Process Deviations and Photoresist Stripping on Contact Yield of Copper Dual Damascene Metallization", Journal of The Electrochemical Society, 149 (12) G656-G660 (2002), pp. G656-G660.

Jackson, "Classical Electrodynamics", John Wiley & Sons, Inc., (month unavailable), 1967, pp. 222-226.

Paquin, "Properties of Metals", Handbook of Optics, vol. II, McGraw-Hill, Inc., (month unavailable), 1995, pp. 35.3-35.7.

Rosencwaig et al. "Detection of Thermal Waves Through Optical Reflectance", Appl Phys. Lett. 46, Jun. 1985, pp. 1013-1015.

Rosencwaig, "Thermal-Wave Imaging", SCIENCE, vol. 218, No. 4569, Oct. 1982, pp. 223-228.

Opsal et al. "Thermal-Wave Detection and Thin-Film Thickness Measurements with Laser Beam Deflection", Applied Optics, vol. 22, No. 20, Oct. 1983, pp. 3169-3176.

Rosencwaig, "Thermal Wave Characterization and Inspection of Semiconductor Materials and Devices", Chapter 5 (pp. 97-135) of Photoacoustic and Thermal Wave Phenomena in Semiconductors, North Holland (month unavailable) 1987.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, (month unavailable) 1990.

J. Kolzer et al "Thermal Imaging and Measurement Technqiues for Electronic Materials and Devices" Microelectronic Engineering, vol. 31, 1996 (month unknown) pp. 251-270.

C. Martinsons et al. "Recent progress in the measurement of thermal properties of hard coatings" Thin Solid Films, vol. 317, Apr. 1998, 455-457.

Bristow, Thomas C. and Dag Lindquist, "Surface Measurements With A Non-Contact Nomarski-Profiling Instrument", Interferometric Metrology, SPIE vol. 816, Aug. 1987, pp. 106-110.

Walter G. Driscoll and William Vaughan, "Handbook of Optics", 1978, pp. 8-42, 8-43, 8-107, and 10-72 to 10-77.

Charles Kittel, "Introduction to Solid State Physics", Fourth Edition, John Wiley & Sons, published prior to Mar. 1, 2002, pp. 262-264.

Rolf E. Hummel, "Electronic Properties of Materials, An Introduction For Engineers", published prior to Mar. 1, 2002, pp. 137-145.

H.S. Carslaw and J.C. Jaeger, "Conduction of Heat in Solids", Second Edition, published prior to Mar. 1, 2002, pp. 64-66.

A. Rosencwaig, "Thermal Wave Measurement of Thin-Film Thickness", 1986 American Chemical Society, pp. 182-191.

A. Rosencwaig et al., "Thin-Film Thickness Measurements with Thermal Waves", Journal De Physique, Oct. 1983, pp. C6-483-C6-489.

S. Ameri et al., "Photo-Displacement Imaging", Mar. 30, 1981, pp. 337-338.

L. Chen et al., "Thermal Wave Studies of Thin Metal Films Using the Meta-Probe-A New Generation Photothermal System" 25th Review of Progress in QNDE, Snowbird, UT Jul. 19-24, 1998, pp. 1-12.

P. Alpern and S. Wurm, "Modulated Optical Reflectance Measurements on Bulk Metals and Thin Metallic Layers", J. Appl. Phys. 66(4), Aug. 15, 1989, pp. 1676-1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp. 120-131.

A. Rosencwaig, "Process Control In IC Manufacturing With Thermal Waves", Review of Progress in Quantitative Nondestructive Evaluation, vol. 9, 1990, pp. 2031-2037.

B.C. Forget et al., "High Resolution AC Temperature Field Imaging", Electronic Letters Sep. 25, 1997, vol. 33, No. 20, pp. 1688-1689.

C. Paddock et al., "Transient Thermoreflectance from Metal Films", May 1986 vol. 11, No. 5, Optical Letters, pp. 273-275.

C. Paddock et al., "Transient Thermoreflectance from Metal Films", J. Appl. Phys. 60(1), Jul. 1, 1986, pp. 285-290.

Per-Eric Nordail et al. "Photothermal Radiometry", Physica Scripts, vol. 20, 659-662, 1979.

A. Rosenwaig, "Thermal Wave Monitoring and Imaging of Electronic Materials and Devices", pp. 73-109.

A. Rosenwaig, "Applications of Thermal-Wave Physics to Microelectronics", VLSI Electronics, Microstructure Science vol. 9, 1995, pp. 227-288.

W. Lee Smith et al., "Voids, Notches and Microscracks in A1 Metallization Detected by Nondestructive Thermal Wave Imaging", Jun. 23, 1989, pp. 211-221.

W. Lee Smith, "Nondestructive Thermal Wave Imaging of Voids & Microcracks in Aluminum Metallization", 1989 WLR Final Report, pp. 55-68.

W. Lee Smith, "Direct Measurement of Stress-Induced Void Growth by Thermal Wave Modulated Optical Reflectance Imaging", 1991 IEEE/IRPS, pp. 200-208.

W. Lee Smith, "Evaluating Voids and Microcracks in A1 Metalization", Semiconductor International, Jan. 1990, pp. 232-237.

C. G. Welles et al., "High-Resolution Thermal Wave Imaging of Surface and Subsurface Defects in IC Metal Lines", Materials Research Society, SF Marriott, Apr. 27-May 1, 1992, pp. 1187-1191.

L. Fabbri et al., "Analysis of Local Heat Transfer Properties of Type-cast AIN Cermaics Using Photothermal Reflectance Microscopy", 1996 Chapman & Hall, pp. 5429-5436.

L. Chen et al., "Meta-Probe: A New Generation Photothermal System For Thin Metal Films Characterization" (believed to be prior to Mar. 1, 2002).

L. Chen et al., "Thermal Wave Studies of Thin Metal Films and Structures", (believed to be prior to Mar. 1, 2002).

R. S. Sharpe, Research Techniques in Nondestructive Testing vol. VII, Academic Press 1984, pp. 158-365.

R. L. Thomas et al., "Thermal Wave Imaging For Nondestructive Evaluation" 1982 Ultrasonic Symposium, pp. 586-590.

G. Slade Cargill III, "Electron-Acoustic Microscopy", Physics Today, Oct. 1981, pp. 27-32.

A. Rosencwaig, "Thermal Wave Microscopy", Solid State Technology, Mar. 1982, pp. 91-97.

Eric A. Ash, "Acoustical Imaging" vol. 12, Plenium Press, Jul. 19-22, 1982, pp. 61-65.

Chung Wah See and Mehdi Vaez-Iravani, "Differential amplitude scanning optical microscope: theory and applications", Applied Optics vol. 27, No. 13, Jul. 1, 1988, pp. 2786-2792.

* cited by examiner

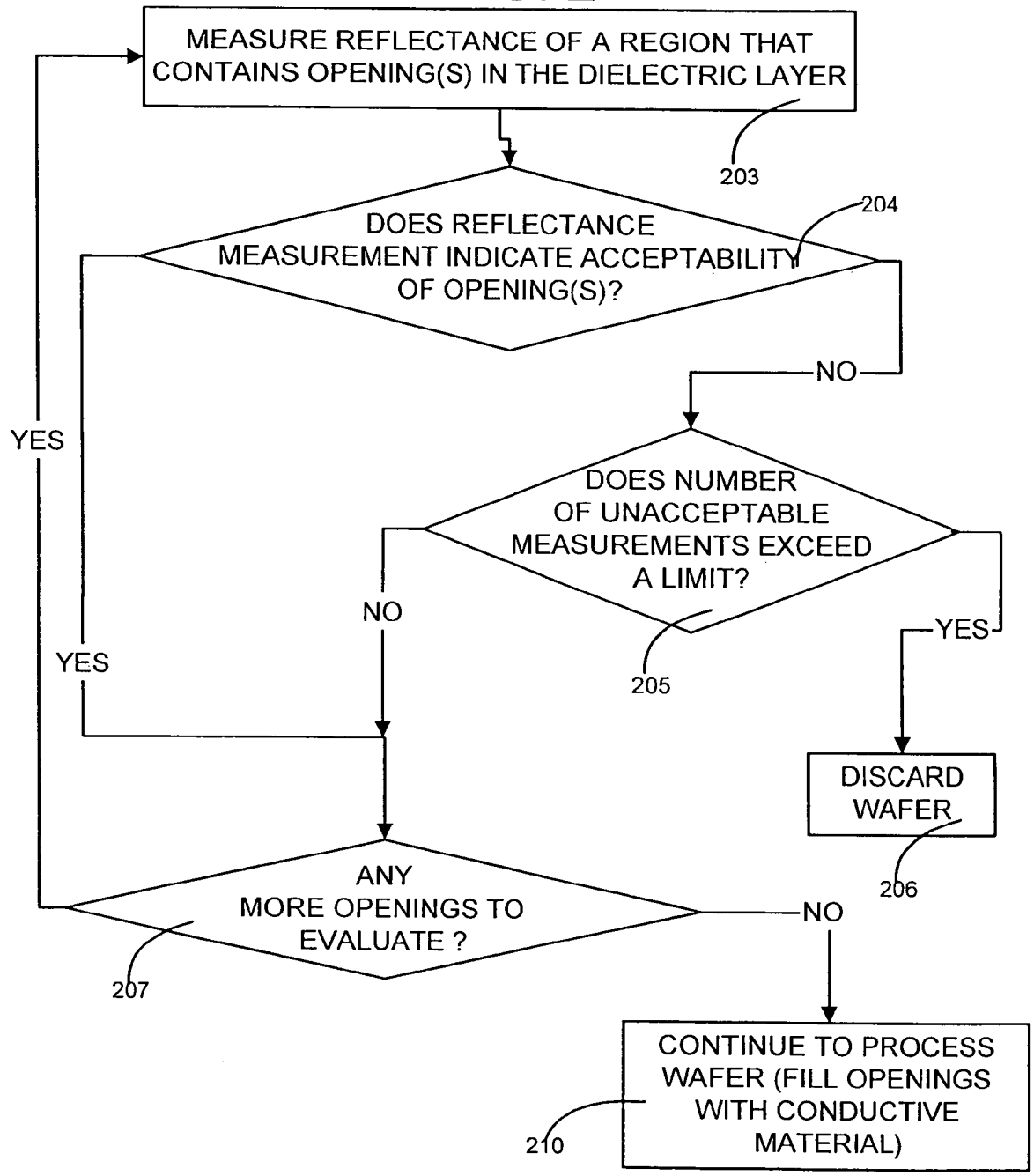

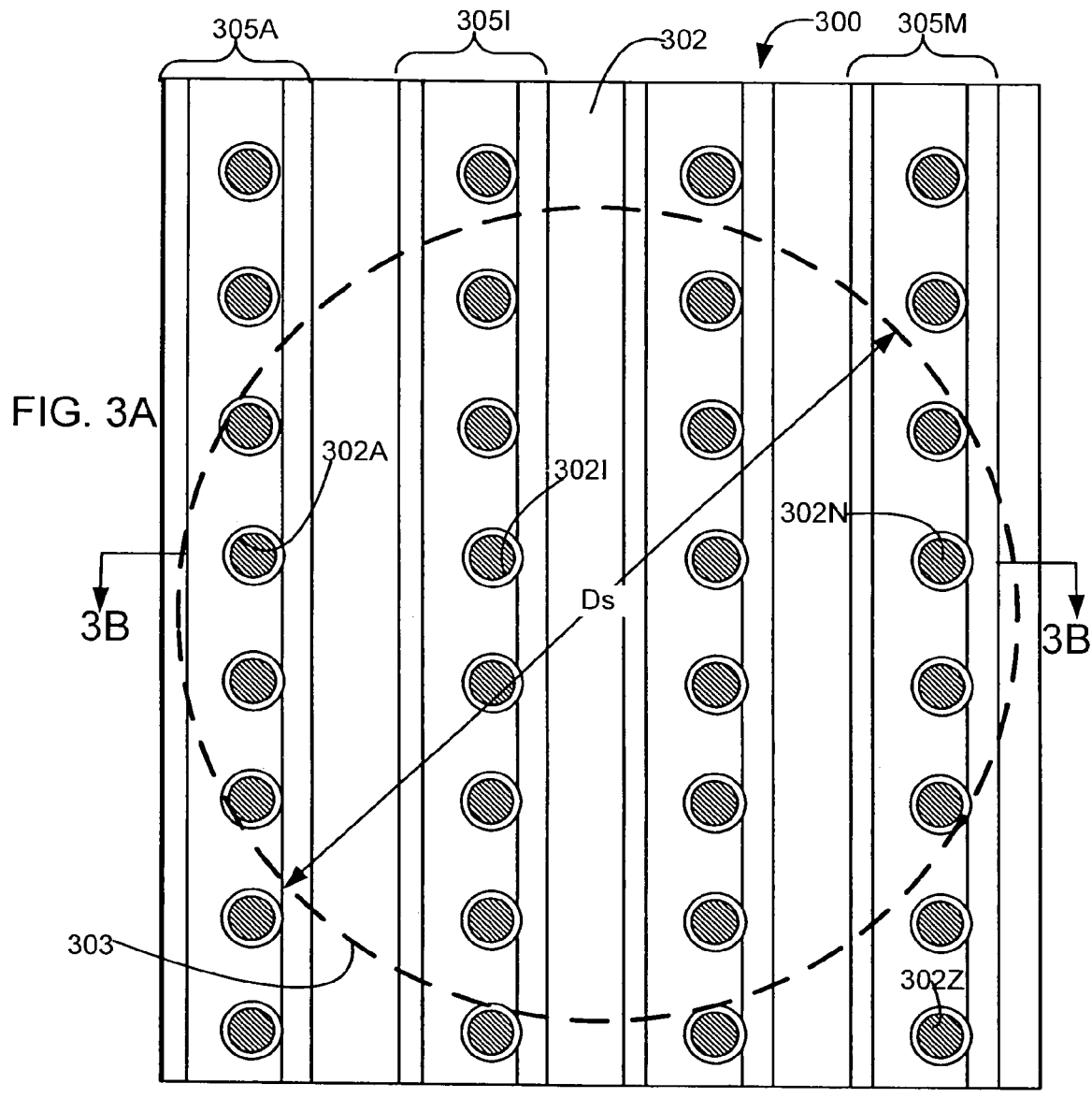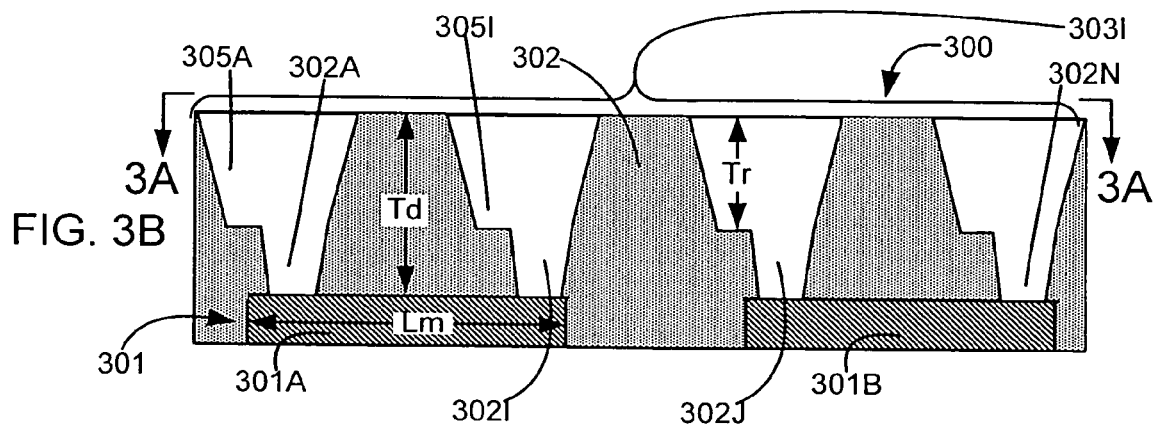

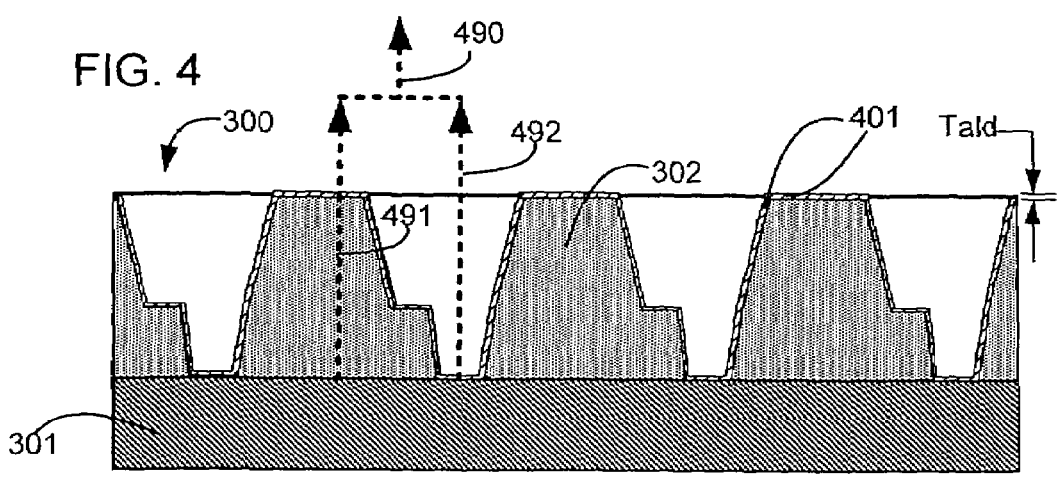
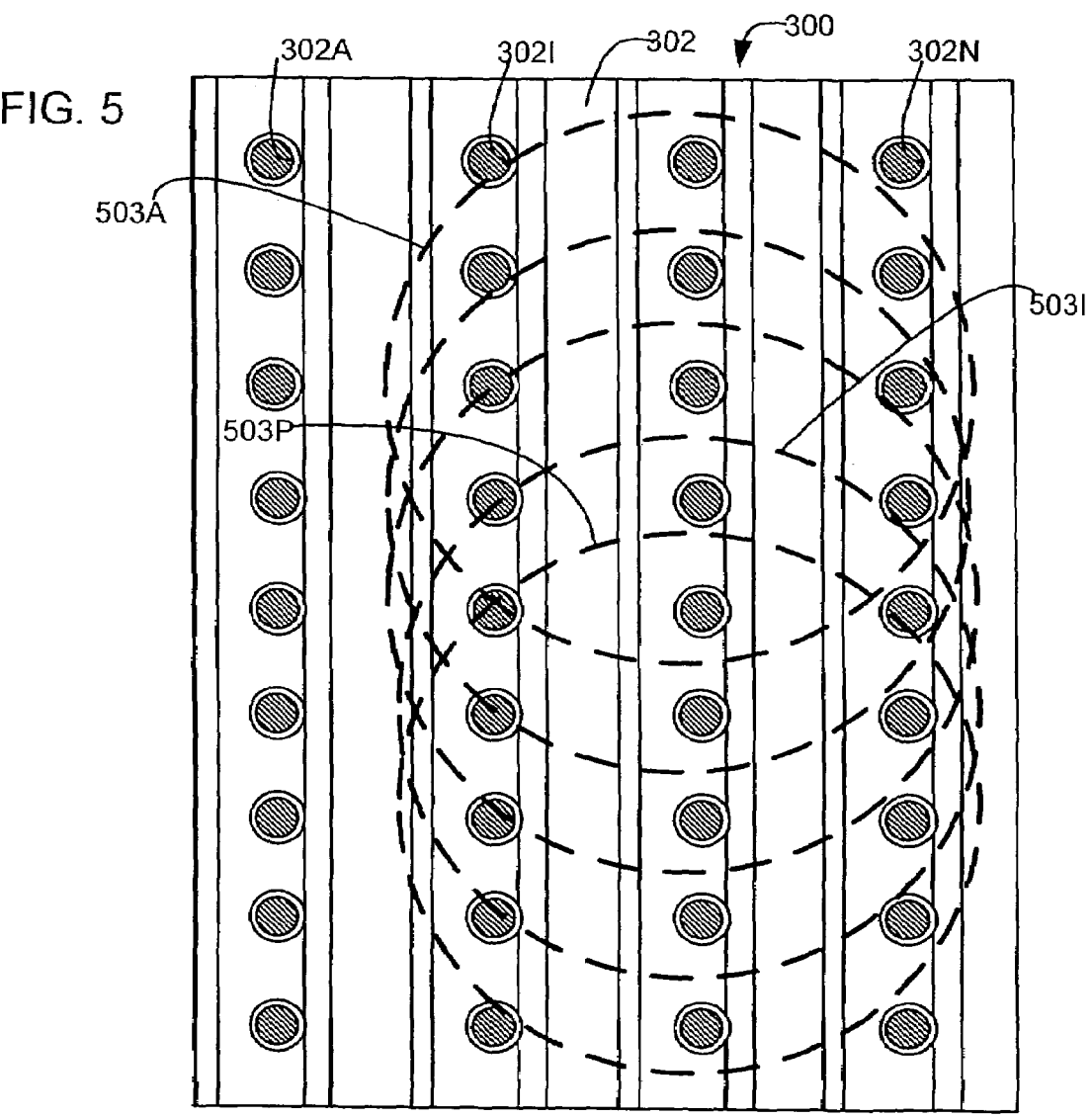

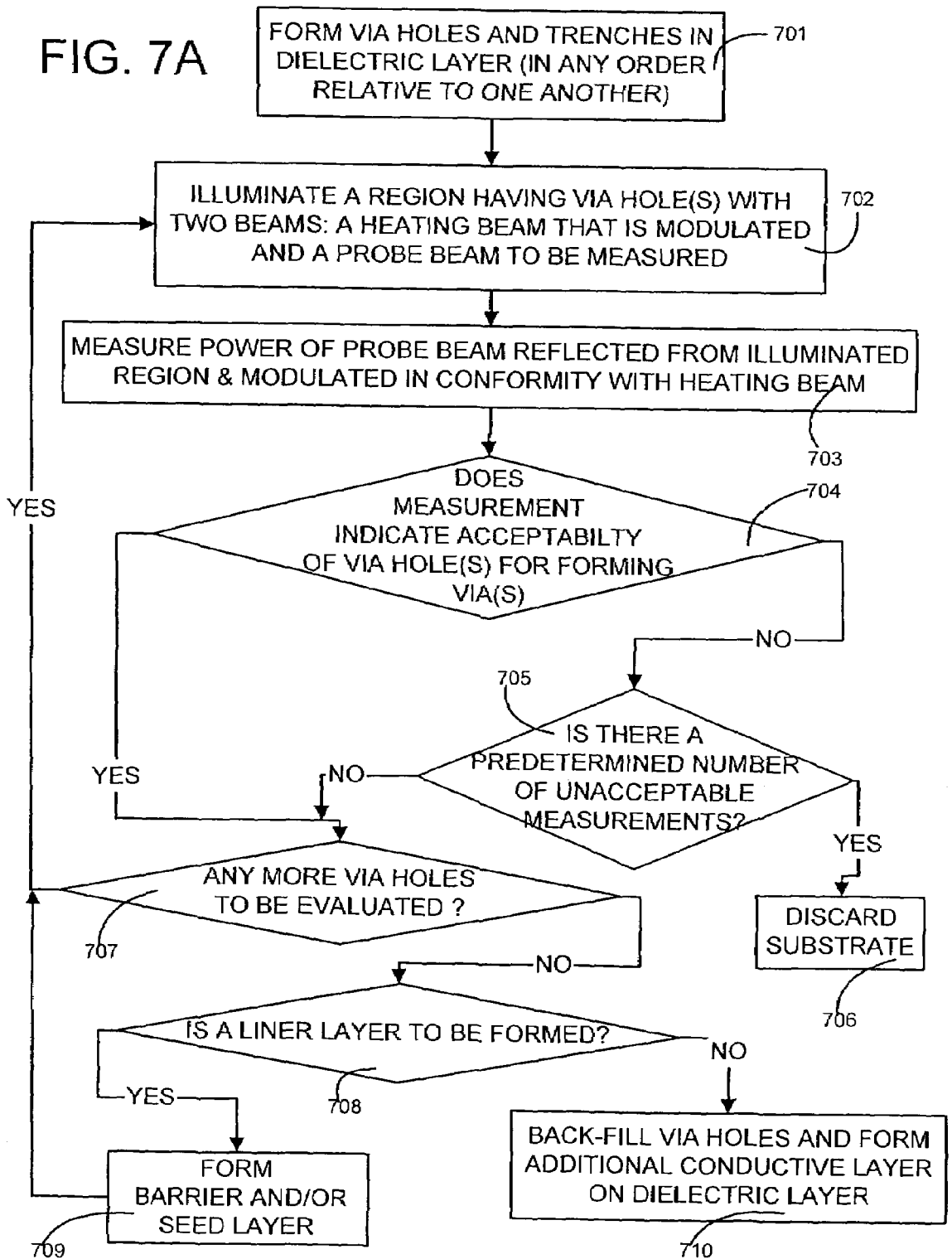

EVALUATION OF OPENINGS IN A DIELECTRIC LAYER

BACKGROUND

The semiconductor industry is now forming copper interconnects between two metal layers in a semiconductor wafer by a damascene process. In a damascene process, openings are formed in a nonconductive layer (also called "dielectric layer") followed by inlay of copper to form metal lines and/or vias. The damascene process is used to form copper interconnects because traditional plasma etch techniques cannot be used to etch copper (e.g. because copper does not form a volatile by-product of the type formed by aluminum). Moreover, a traditional dielectric layer of $SiO_2$ is being replaced with one or more materials having a lower dielectric constant k. Such new processes are used in fabrication of memory devices as well as logic devices.

FIG. 1A illustrates, in a cross-sectional view, a wafer 100 that is undergoing conventional fabrication, e.g. for formation of via holes through a dielectric layer. Specifically, as shown in FIG. 1A, wafer 100 includes a metal layer 101, which may or may not be patterned into lines (also called "traces"). In addition, wafer 100 also includes a dielectric layer 102 (also called "interlayer dielectric" or "ILD") that is located over metal layer 101. A photo-resist layer 103 is also shown in FIG. 1A, which has been deposited on dielectric layer 102, and is exposed at certain sites to form holes 103A-103N.

The bottoms of holes 103A-103N (FIG. 1B) are used (with layer 103 as a mask) to etch away dielectric layer 102, up to underlying metal layer 101, thereby to form a corresponding number of via holes 102A-102N that pass all the way through layer 102. The just-described process of forming through holes 102A-102N sometimes leaves residue 104 in a hole 102I, which may, for example, be a chemical or copper oxide. Presence of residue may increase the resistance of a via 105I (FIG. 1C) when it is formed in hole 102I, or affect reliability of via 105I (as compared to other vias 105A and 105N).

Even in the absence of residue, vias 105A-105N in holes 102A-102N may not be formed uniformly, e.g. if corresponding holes 102A-102N are not formed of identical diameters. A via that is too large in diameter may become shorted to an adjacent structure, while a via that is too small in diameter may have too much resistance, or sometimes the via may not be formed uniformly throughout the depth of the via hole.

U.S. Pat. No. 6,054,868 granted to Borden, et al. on Apr. 25, 2000 (and incorporated by reference herein in its entirety) teaches that conductivity of a dielectric layer that is located underneath a conductive layer may be measured by: (1) focusing a heating beam on the heated a region (also called "heated region") of the conductive layer (2) modulating the power of the heating beam at a predetermined frequency that is selected to be sufficiently low to ensure that at least a majority (preferably all) of the generated heat transfers out of the heated region by diffusion, and (3) measuring the power of a probe beam that is (a) reflected by the heated region, and (b) modulated in phase with modulation of the heating beam. Diffusion of heat occurs in the just-described method, by conduction under steady state conditions, eliminating the creation of a thermal wave as described in U.S. Pat. No. 5,228,776. Note that the dielectric layer described in U.S. Pat. No. 6,054,868 is (a) unpatterned and (b) located underneath the conductive layer.

U.S. Pat. No. 6,040,936 granted to Kim is incorporated by reference herein in its entirety. This patent discloses a metal film having a periodic array of sub-wavelength-diameter holes provided therein, and a supporting layer. At least a portion of the supporting layer has a selectively variable refractive index, the selectively variable refractive index portion being substantially adjacent to the metal film such that the metal film and the supporting layer comprise a perforated metal film unit. Selective variation of the refractive index of the selectively variable refractive index portion modulates the intensity of the light transmitted through the perforated metal film unit without substantially changing the direction of the light. Note that U.S. Pat. No. 6,040,936 describes the sub-wavelength-diameter holes as being formed in a metal film which is not a dielectric film. Moreover, the structure by Kim is not disclosed as being formed during fabrication of integrated circuit (IC) dies in a semiconductor wafer. Also, as the perforated layer is metal, one would expect that there would be a strong signal from that layer that would overwhelm any signal from the bottoms of the holes.

See also U.S. Pat. No. 6,734,968 granted to Wang on May 11, 2004 that is incorporated by reference herein in its entirety. This patent describes two phase modulators or polarizing elements employed to modulate the polarization of an interrogating radiation beam before and after the beam has been modified by a sample to be measured. Radiation so modulated and modified by the sample is detected and up to 25 harmonics may be derived from the detected signal. The up to 25 harmonics may be used to derive ellipsometric and system parameters, such as parameters related to the angles of fixed polarizing elements, circular deattenuation, depolarization of the polarizing elements and retardances of phase modulators. The above-described self-calibrating ellipsometer may be combined with another optical measurement instrument such as a polarimeter, a spectroreflectometer or another ellipsometer to improve the accuracy of measurement and/or to provide calibration standards for the optical measurement instrument. The self-calibrating ellipsometer as well as the combined system may be used for measuring sample characteristics such as film thickness and depolarization of radiation caused by the sample.

SUMMARY

Patterning of a dielectric layer of a semiconductor wafer that is undergoing fabrication is evaluated, in accordance with the invention, by measuring reflectance of a region in the wafer which contains the patterning. The reflectance measurement contains a contribution of light reflected from inside of opening(s) in the dielectric layer (also called "opening" contribution) and another contribution of light reflected from outside of the opening(s). The inventors note that the relative size of these two contributions changes, depending on a number of factors that affect suitability of the dielectric layer for future use in inlay of a conductive material to form damascene structure(s). Therefore, a reflectance measurement that includes both contributions, is used in several embodiments, as a measure of acceptability (e.g. as a cleanliness measure after a clean step) of a patterned dielectric layer, e.g. to decide whether or not the patterned dielectric layer is to be subjected to further fabrication, in some embodiments by forming conductive element(s) in the opening(s).

Some embodiments perform reflectance measurements while heating a conductive material (such as metal, e.g. copper) at the bottom of openings of a patterned dielectric.

In several such embodiments, a heating beam is modulated in conformance with a sinusoidal waveform at a predetermined frequency and illuminates a spot on the wafer, while power of a probe beam as reflected from the illuminated spot is measured at the predetermined frequency. The predetermined frequency in some embodiments is selected to be sufficiently low to ensure that at least a majority of heat is transferred out of the conductive material in the illuminated region, not by a thermal wave but by thermal diffusion. In one embodiment, the diameter of the probe beam is on the order of a dimension of an opening, while in most embodiments the probe beam diameter is larger, e.g. several times an opening's dimension.

Note that instead of using a sinusoidal waveform in modulating the heating beam, a waveform of any predetermined shape (e.g. square shape) may be used, depending on the embodiment. In non-sinusoidal modulations, the predetermined waveform may be selected to include frequency components which are selected to be sufficiently low to avoid creation of a thermal wave. Such multiple frequencies may be included in a chirp or a phase code modulation of the heating beam.

Some embodiments have a trace of continuous metal (in which case a majority of heat flows out of the illuminated spot by conduction through the metal), while other embodiments have a number of isolated metal elements that may be equal to or smaller than the spot size (in which case heat flows out of the illuminated spot primarily by diffusion through the surrounding dielectric layer). Each metal element is located at the bottom of two or more via holes, in order to be used to interconnect vias that are to be formed therein. During reflectance measurement of the type described herein, the temperature of such isolated metal elements rises to a level greater than a corresponding temperature of continuous metal. This is because heat that is dissipated out of an illuminated spot from isolated metal elements is much less, as compared heat dissipated by a continuous metal trace.

A heating beam's wavelength is preselected, in some embodiments, to ensure high reflectance of a conductive material (such as copper) located (or intended to be located) at the bottom of the openings. In several such embodiments, a very high reflectance of the conductive material (when clean) is ensured, by deliberately selecting the heating beam's wavelength to be within a predetermined band specific to the conductive material. The predetermined band is identified in some embodiments of the invention in conformance with Drude's definition of a "relaxation region". For example, to evaluate structures that contain copper as the buried layer, certain embodiments use a heating beam of 830 nm wavelength and this wavelength is selected because it is within the relaxation region of copper, and provides a reflectance of 97%. In this example, only 3% of the incident energy is absorbed. In this manner, in several embodiments, a structure of patterned dielectric with underlying metal (either continuous trace or isolated elements) is heated with light of a selected wavelength that is sufficiently large to ensure absorption at least an order of magnitude smaller than reflection. Such a difference in reflectance and absorptance provides an amplification of sensitivity in an acceptability measure obtained from measuring reflectance of structures that have highly reflective conductive materials (such as metals) located under a patterned dielectric layer that is substantially transparent (e.g. more than 95% transmissive).

In other embodiments, a heating beam of wavelength longer than the relaxation wavelength is used, e.g. corresponding to the "Hagen-Rubens" region, where the reflectance is also much greater than the absorption.

The above-described wavelength is selected for the heating beam even if the features to be evaluated are of a smaller dimension that the wavelength. For example, cleanliness of via holes of sub-wavelength diameter is evaluated by reflectance measurement in many embodiments. Inventors note that the contribution of openings in such a reflectance measurement is affected by the presence of residue in the opening(s) and by a change in dimension of the opening(s). For example, presence of residue at the bottom of a via hole changes (either decreases or increases) the reflectance measurement, due to a corresponding change in the contribution of openings. Hence changes in the reflectance measurement detect such residue presence, in some embodiments. Moreover, a change in the size of openings also changes the openings' contribution, again changing the reflectance measurement, which is again detected in some embodiments. In some embodiments, further processing is discontinued (e.g. wafers are discarded) when the measured reflectance falls below a predetermined limit, regardless of the source of the drop in reflectance (e.g. reduction in via hole diameter and/or presence of residue).

Each illuminated spot in which a reflectance measurement is to be made in accordance with the invention is selected to be (a) a region that partially or completely contains the patterning, and (b) of size sufficiently small for a change, that is to be detected, to affect the reflectance measurement. For example, spot size is made in some embodiments to be several times larger than a via hole and to cover a number of via holes. In many embodiments, the ratio of spot size to via diameter is large, e.g. 3-5 times in some embodiments and 10-50 times in other embodiments. Such embodiments evaluate multiple via holes or other such openings as a group in a single measurement at a single spot. The specific size of a spot in which reflectance is measured in some embodiments is preselected based on several factors, such as reflectance in a via hole relative to the reflectance of the surrounding dielectric layer (e.g. if a conductive layer at the bottom of an opening is exposed), and the signal to noise ratio of the measurement.

BRIEF DESCRIPTION OF THE FIGURES

FIG. 2 illustrates, in a flow chart, acts performed in some embodiments of the invention to evaluate openings in a dielectric layer of a semiconductor wafer.

FIGS. 3A and 3B illustrate, in a plan view and a cross-sectional side view respectively, a region of a wafer having isolated metal elements underneath a patterned dielectric layer whose reflectance is measured in some embodiments of the invention.

FIG. 4 illustrates, in a cross-sectional side view, some embodiments that evaluate openings having a liner, using a heating beam and a probe beam.

FIG. 5 illustrates, in a plan view, a series of overlapping spots at which measurement of reflectance is made in some embodiments.

FIG. 7A illustrates, in a flow chart, acts performed in some embodiments of the invention to create and evaluate a patterned dielectric layer.

DETAILED DESCRIPTION

Figure 1A:
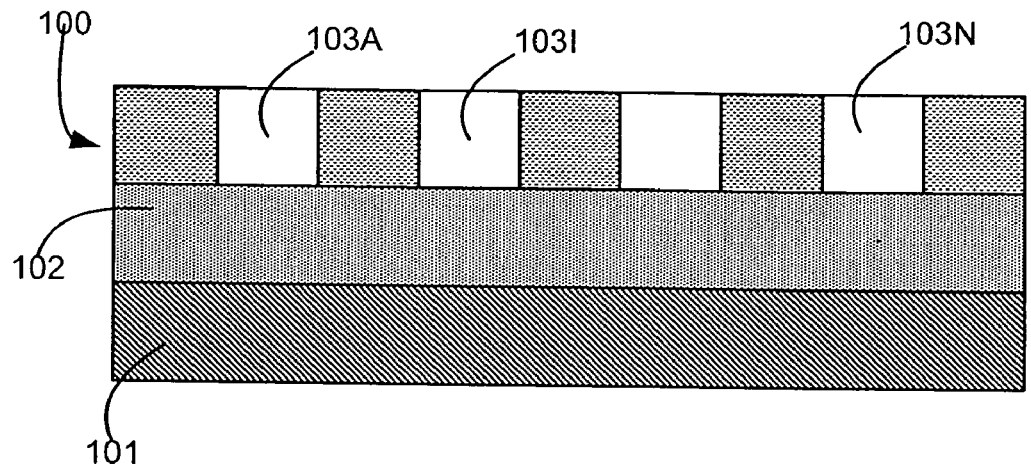
FIGS. 1A-1C illustrate, in cross-sectional views, various features of a prior art wafer during fabrication.

Some prior art methods evaluate conductive structures (such as conductive lines and conductive vias) after they are formed. Although a scanning electron microscope can view structures as they are formed, SEMs have certain limitations. For example, SEMs charge dielectrics and are therefore limited in their ability to inspect structures after dielectric etch. Also, SEMs cannot see certain thin residues that effect via interconnections. Another limitation is that a SEM performs a vacuum measurement, requiring a vacuum chamber that adds significant cost. There appears to be no prior art method known to the inventors that evaluates suitability of a pattern in a dielectric layer, in a semiconductor fabrication facility (also called "fab"), as a part of a process of fabricating a wafer.

Many embodiments in accordance with the invention evaluate a pattern itself, of a dielectric layer, that is formed during a damascene process, for future use in inlay of a conductive material. Specifically, some embodiments measure reflectance in a region of the dielectric layer that has openings of a predetermined shape, such as via holes and trenches that are formed in a semiconductor wafer during the damascene process. Evaluation of openings themselves in accordance with the invention is commercially valuable, because it finds problems at an earlier stage in wafer fabrication, before it is possible to test such structures electrically. Early-stage identification of problems, e.g. by reflectance measurement after patterning to create openings in a dielectric layer but before inlay of copper, is used to improve yield in many embodiments of the invention.

Openings in a dielectric layer (e.g. of a wafer undergoing fabrication for the production of IC dies, i.e. production wafers) are evaluated in many embodiments of the invention by measuring reflectance of a region of the dielectric layer that contains the opening(s), as per act 203 (FIG. 2). In some embodiments, the openings are typically via holes 302A-302N (FIGS. 3A and 3B) that pass all the way through a thickness Td of dielectric layer 302. In such embodiments, reflectance of an underlying conductive layer 301 (e.g. formed of isolated metal elements 301A and 301B at the bottom of FIG. 3B) affects a reflectance measurement in region 303I. Note that in the structure of FIG. 3B, metal elements 301A and 301B are isolated from one another and also isolated from all other metal structures. Example values of dimensions are Td=0.5 um, Tr=0.3 um and Wt=0.12 um (FIG. 3D). Also an example value of the thickness of conductive layer 301 is 0.3 um.

Such isolated metal elements 301A and 301B may have a length Lm (e.g. 0.4 µm) that is smaller than the diameter Ds (e.g. 1-2 µm) of spot 303I (e.g. 2 to 5 times smaller) in some embodiments. In such embodiments, heat flows out of illuminated spot 303I primarily by diffusion through the surrounding dielectric layer. Note that the metal elements 301A and 301B have a sufficiently large cross-section to be used in reflecting the incident light. From this perspective, the metal elements are ¼ wavelength (i.e. one-fourth wavelength) to ½ wavelength (i.e. one-half wavelength) long, depending on the embodiment.

Each metal element 301I is located at the bottom of two or more via holes, for future use in interconnecting vias that are to be formed therein. For example, metal element 301A is located at the bottom of via holes 302A and 302I in which interconnect vias are to be formed by inlay of a conductive material (see FIG. 1C). During reflectance measurement, the temperature of each isolated metal element 302I that is contained in spot 303I rises to a level greater than a corresponding temperature of continuous metal trace 301 (see bottom of FIG. 3C). This is because heat that is dissipated out of an illuminated spot 303I from isolated metal elements 301A and 301B is much less, as compared heat dissipated by continuous metal trace 301. For example, the isolated metal links may rise to a temperature that is a few 10s of degrees greater than the temperature rise of a corresponding trace that forms a continuous line through the illuminated region.

Via holes 302A-302N shown in FIGS. 3A and 3B are located at the bottom of trenches 305A-305M. Depending on the wafer fabrication process used, via holes 302A-302N may be formed in dielectric layer 302 initially, followed by formation of trenches 305A-305M (after via hole formation). Specifically, the wafer is coated with a "via" photoresist and lithographically patterned for via formation, followed by an anisotropic etch to etch down through the interlayer dielectric layer 302, up to a barrier layer (not shown in FIG. 3B; e.g. formed of amorphous SiC:H or silicon nitride) that covers and protects conductive layer 301. Note that the barrier layer is formed before the just-described etching.

Thereafter the via holes are filled with a temporary filler material, called a BloK layer (e.g. for barrier low-k). The BloK layer used in some embodiments is a film deposited by chemical vapor deposition. A key aspect of using the BloK layer is that it is removed with an etch process, and the etch process sometimes leaves a residue at the bottom of the via hole that is difficult to detect. Therefore methods of the type described herein detect BloK residue (the 60%/40% etch time data in FIGS. 7C, D, E, F are for measurements immediately following the BloK open etch). The wafer is then re-patterned with photoresist to define trenches. The trenches are etched to a depth defined either by the time of the etch or by an etch-stop layer (not shown in FIG. 3A). Finally, the BloK layer is selectively etched away to re-open the via holes to the copper.

Note that in the previous paragraph, the terms "via" photoresist and "trench" photoresist are used merely to distinguish between the two etching steps, and the composition of the photoresist that is actually used in these steps may be either the same or different, depending on the embodiment.

Note that in other embodiments such acts may be reversed, with trenches 305A-305M being formed first (at which time there are no via holes), followed by formation of via holes 302A-302N at the bottom of the trenches. A reflectance measurement of the type described herein may be used regardless of the specific order of acts used to form a pattern of openings in a dielectric layer (see the pattern formed by holes 302A-302Z and trenches 305A-305M in FIGS. 3A-3B).

As noted above, a reflectance measurement in region 303I in wafer 300 (FIG. 3A) is affected by the reflectance of a conductive layer 301 (FIGS. 3B and 3C) located underneath dielectric layer 302. Note that conductive layer 301 can be any one of a number of conductive layers that may be present in a wafer 300 at any time during semiconductor fabrication, and before the wafer 300 is diced to form integrated circuit (IC) dies. Specifically, layer 301 can be one level among any of a number of levels in a multi-level interconnect in wafer 300. Note that such a reflectance measurement is not significantly affected by dielectric absorption of light, at least because the dielectric absorption is small to begin with, and is reasonably well controlled in semiconductor processes normally used for fabricating layer 302. Furthermore, comparison to a reference structure removes (or minimizes) the effect of local non-uniformities in dielectric layer 302.

Figure 3C:
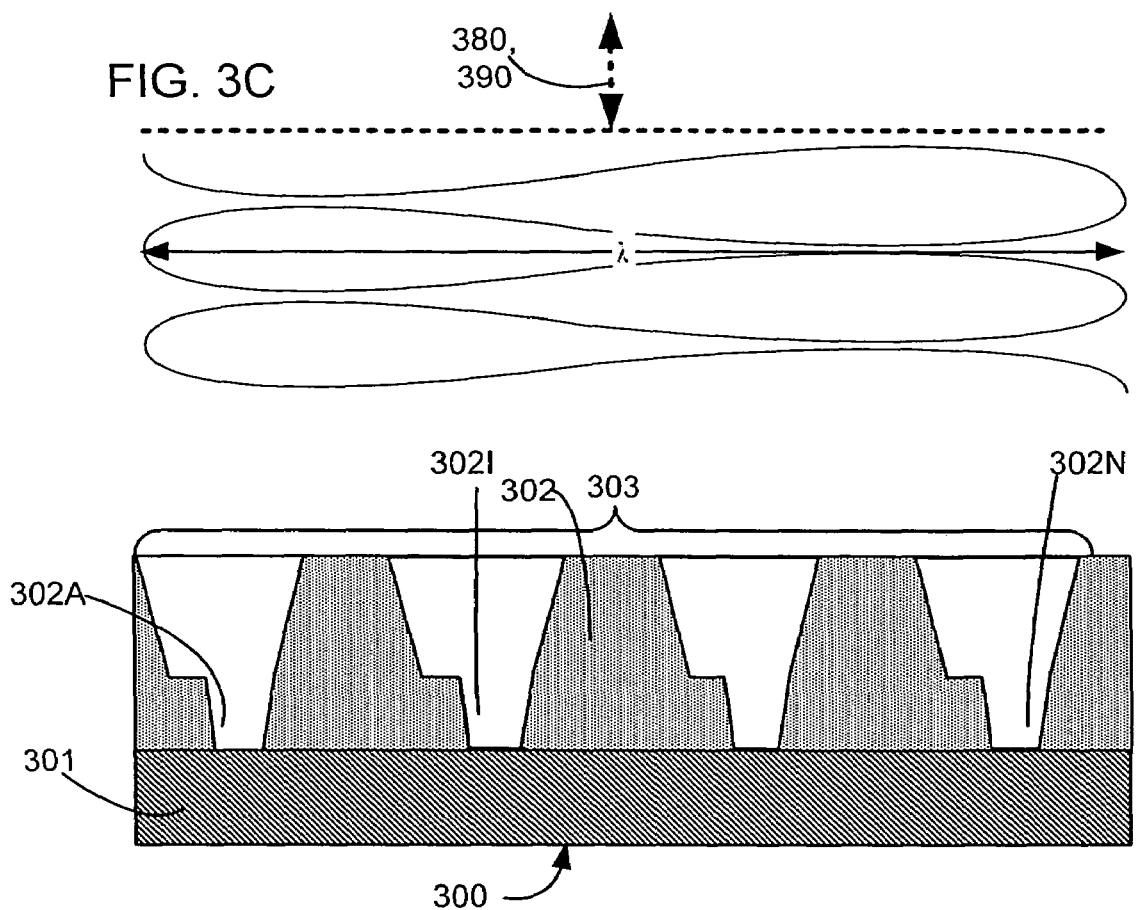
FIG. 3C illustrates, in a cross-sectional side view, reflectance measurement of another wafer wherein the metal layer underlying the patterned dielectric is continuous.
Figure 3D:
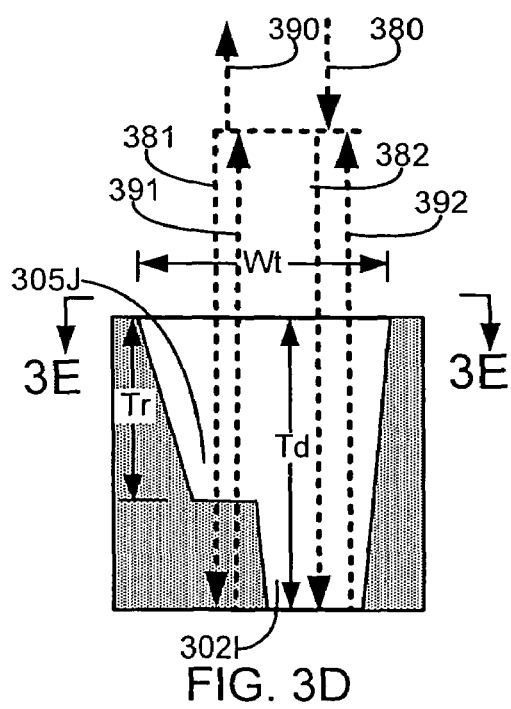
FIGS. 3D and 3E illustrate, in a cross-sectional side view and a plan view respectively of an enlarged portion of FIG. 3C a component of light that travels all the way through an opening in the dielectric layer (also called "opening" contribution), and another component that travels at least partway through a dielectric layer, in certain embodiments of the invention.

Referring to FIG. 3C, when light 380 is incident in region 303I, a reflectance measurement is in fact indivisible relative to the openings in region 303I because wavelength $\lambda$ of incident light 380 (e.g. 0.5 µm to 3 µm) is several times (e.g. 3-20 times) greater than diameter Dv (e.g. 0.15 µm) of a via hole 302I. Hence, one may not expect such a reflectance measurement to be sensitive to changes in dimension of via hole 302I and/or presence of residue, due to the large wavelength of incident (and reflected) light. Applicants have found that the reflectance measurement is sensitive to such changes even though the via holes are of sub-wavelength dimension. One explanation is to conceptually model a superposition (of reflectance) of two components 381 and 382, wherein component 381 (also called "dielectric component") refers to light incident (and reflected) outside of hole 302I and component 382 (also called "via-hole component") refers to light incident (and reflected) through the entire length of hole 302I. The relative contribution of the "via-hole component" 381 in the (single indivisible) reflectance measurement is given by the ratio of via hole area to spot area. For dense structures, this ratio can be large, e.g. 25% to 50%.

In the above-described conceptual model, component 382 of the incident light travels through the entire length of hole 302I and reaches conductive layer 301 that is exposed at the bottom of hole 302I. Depending on the reflectance of conductive layer 301, a majority of this component 382 (e.g. over 90%) is reflected back as light 392 (FIG. 3B) through the entire length of hole 302I (also called "via-hole component"). In addition, in this conceptual model, dielectric component 381 is incident outside of hole 302I and is also reflected back as light 391 which passes through dielectric layer 302. Note that dielectric component 381 may pass through only a part of dielectric layer 302 or may pass completely through a depth Td of dielectric layer 302. Dielectric component 381 travels through only a part of dielectric layer 302 for example through depth Td–Tr at the bottom of a trench 305J (see FIG. 3D). Reflectance at an interface between dielectric layer 302 and underlying conductive layer 301 is lower than the corresponding reflectance at an interface of layer 301 with air, and hence component 381 is not reflected to the same extent as component 382. Via-hole component 392 forms a sufficiently large portion of the reflectance measurement, to ensure that a change in via diameter and/or presence of residue is easily detected.

Figure 3E:
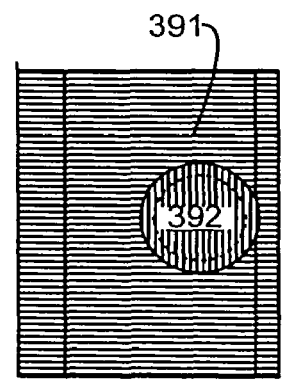

Although two separate components 381 and 382 are illustrated in FIGS. 3D and 3E, they are merely a conceptual model, because as noted above, the incident light's (and reflected light's) wavelength $\lambda$ is larger than the diameter Dv of via hole 303I and also larger than width Wt of trench 305J (see FIG. 3B for these dimensions). The two reflected components 391 and 392 together form reflected light 390 that is measured in accordance with the invention, as the light reflected from region 303I. A change in diameter of via hole 302I affects the reflected light 390 and its measurement, which is detected as per act 204 (FIG. 2). A residue on the surface of metal 301 inside via hole 302I will also affect reflectance, changing it from a value observed for metal without a residue. This residue is typically very thin (a few tens of angstroms), and is not shown in FIGS. 3C and 3D. Instead, see via hole 302K in FIGS. 3F and 3G for an illustration of such residue.

Figure 3F:
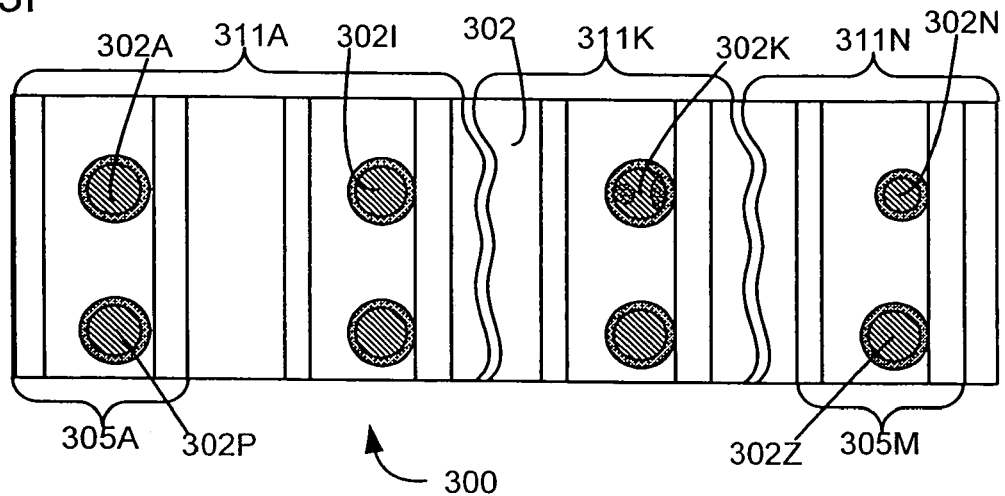
FIGS. 3F and 3G illustrate, in a plan view and a cross-sectional side view respectively, regions of the substrate of FIGS. 3A and 3B from which measurements are compared to identify defects in the openings, such as presence of residue or under-sized openings.
Figure 3G:
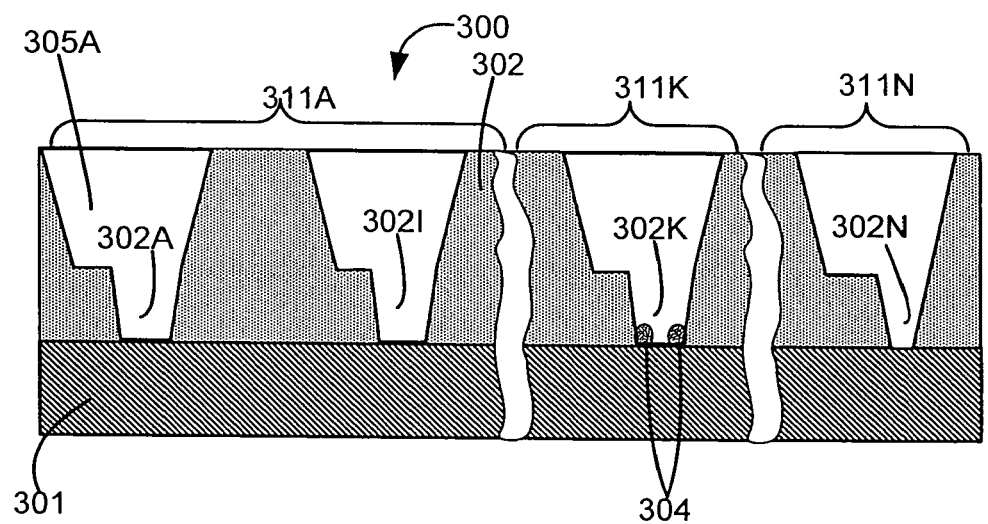

Another example shown in FIGS. 3F and 3G is a decrease (e.g. by 10%) in diameter of a hole 302N (as compared to hole 302I), which correspondingly changes (e.g. by 9%, in case of 90% reflectance) the via-hole component in the reflectance measurement relative to the dielectric component, because of a similar relative change (e.g. by 9%) in via-hole component 392 reflected from inside of hole 302N. Note that the area from which dielectric component 391 is reflected increases due to the decrease in the area from which via-hole component 392 is reflected (because the size of illuminated region 303I remains unchanged—see FIG. 3E). However, in most cases, such increase in dielectric component 391 does not identically offset the decrease in via-hole component 392, due to the difference in reflectance of the conductive and dielectric layers. Therefore, a change in diameter of hole 302N changes the intensity of reflected light 390, which change is detected in some embodiments.

Similarly, presence of residue 304 (see FIG. 3G) reduces the area of conductive layer 301 that is exposed at the bottom of a hole 302K, and hence decreases via-hole component 392. Therefore, presence of residue in hole 302K reduces the intensity of reflected light 390, and such a change is detected in several embodiments as per act 204 (FIG. 2). Such residue may be present over the entire copper layer 301 in the bottom of hole 302K and may affect the copper reflectivity without changing the hole size.

Note that a via hole 302I can have any size relative to the size of illuminated region 303I. However, many embodiments are designed to have tens of via holes (e.g. 20, 30, or 40 holes) illuminated in a spot, because presence of 10s of via holes removes the requirement to carefully align the beam to the via holes, and reduces the granularity of response if there is, say one more or less holes in the illuminated region 303I. In such embodiments, when a problem is found, the methodology may require going back to investigate with FIB cuts to see the cause. Such investigation with FIB cuts becomes less feasible as the number of via holes in the illuminated region 303I increases because the source of the problem is less localized. A practical upper limit, from the standpoint of localizing a problem to a small number of via holes by use of FIB cuts, is several tens of via holes under the spot.

In the embodiment illustrated in FIG. 3A, the reflectance measurement does not resolve individual via holes 302A-302N in the illuminated region 303I, and instead the reflectance measurement indicates an average measure of a dimension of (or residue presence in) the via holes. For example, if a sufficient number of holes 302A-302N have diameters smaller than a predetermined diameter by a sufficient amount, then a measurement of reflected light will be sufficiently different from a reference measurement to be detected (over noise).

Figure 3H:
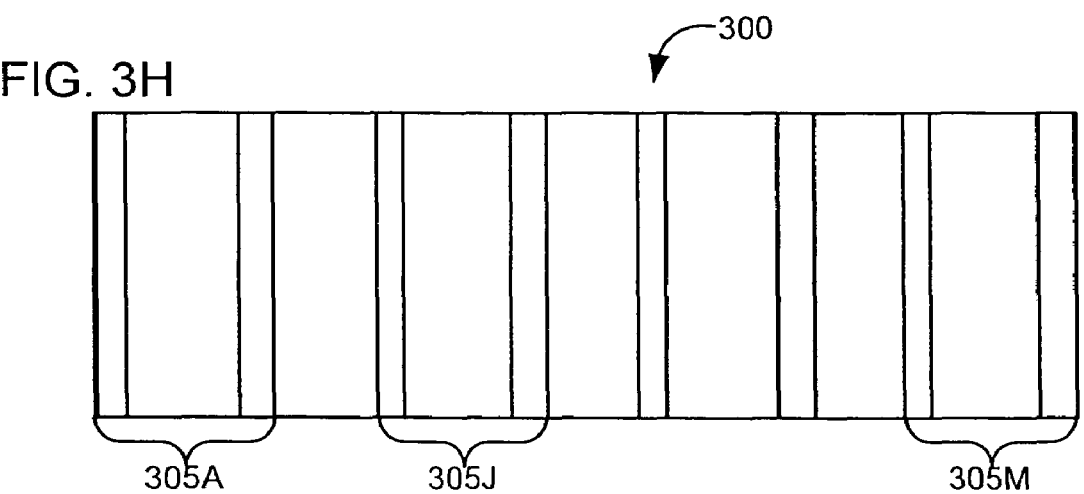
FIGS. 3H and 3I illustrate, in a plan view and a cross-sectional side view respectively, a region of the substrate of FIGS. 3A and 3B that is devoid of via holes that in some embodiments of the invention provides a reference measurement used in normalization.
Figure 3I:
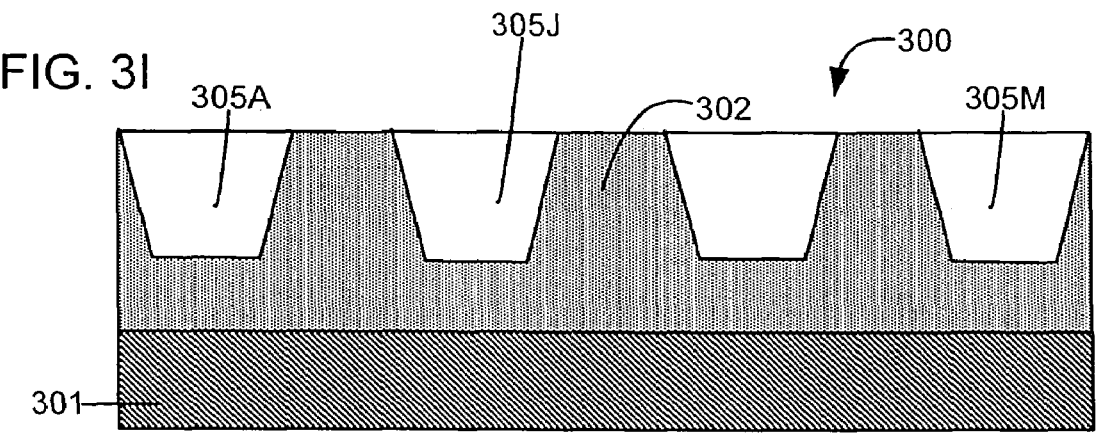

Note that in some embodiments, a reflectance measurement at each location is corrected by use of (e.g. normalized by dividing with) a reference measurement in a corresponding region that is similar or identical in all respects but does not have the openings being evaluated. Normalization reduces (or eliminates) the effect, in the reflectance measurement, of variation in one or more parameters not related to presence of vias, such as global nonuniformity in a wafer. For example, reference measurements to be used for normalization are obtained from a region that has only trenches but no via holes, as illustrated in FIGS. 3H and 3I. Typically, such regions are adjacent to or nearby (with a few tens of microns) to the region with via holes (which is being evaluated by the above-described reflectance measurement), in order to minimize the effect of spatial process non-uniformity.

Figure 3J:
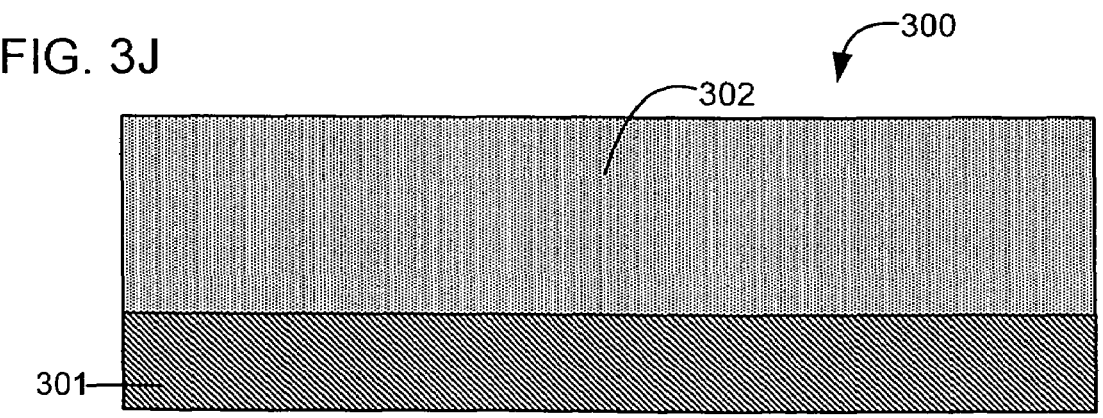
FIG. 3J illustrates, in a cross-sectional side view, a region of the substrate of FIG. 3A that is devoid of via holes that in some embodiments of the invention provides a reference measurement used in normalization.

A reference structure for use in reflectance measurements may take several forms. For example, in some embodiments, a trench-only structure of the type shown in FIGS. 3H and 3I is built as a reference at a location physically adjacent to a structure with via holes in trenches that is currently under evaluation in region 303I. In other embodiments, the reference structure may have no etched pattern (with a dielectric layer located over metal as shown in FIG. 3J), and is compared to a region that has etched via holes. In some embodiments, a reference structure in the form of the trench-only structure illustrated in FIGS. 3H and 3I is obtained prior to formation of via holes, and at least one reference measurement, to be used for normalization is made at that time, and saved for future use (i.e. in dividing a reflectance measurement of region 303I after via holes are formed).

Some other embodiments evaluate openings in the form of trenches only, by performing a reflectance measurement in a trench-only structure of the type shown in FIGS. 3H and 3I and comparing this measurement with a reference measurement made on the structure of FIG. 3J (having no etched patterns). Such measurements are useful in evaluating the uniformity (and suitability) of the trenches in FIGS. 3H and 3I for a subsequent wafer fabrication step (such as via hole formation or copper inlay to form traces of conductive lines). Note that in these embodiments, the openings are formed only part way through thickness Td. Hence, trench (es) 305A-305M of depth Tr are also evaluated in accordance with the invention, by measuring reflectance of a region that contains the trench(es).

While in most embodiments described herein, sub-wavelength features are being evaluated, in one embodiment there is only one via hole under a spot of illumination. This is a measurement mode that requires scanning the beam over the via hole (taking multiple measurements and a longer time), as registration of the spot to the location of the via hole is difficult. Typically, there are multiple vias—say 20—under the spot. In contrast, in sub-wavelength embodiments, via spacing might be 0.4 µm and the spot is about 2 µm in diameter, so there would be 25-30 vias under the spot for this example. This means small errors in registration of the spot to the pattern will have a negligible effect on the signal because of the small inter-via distance compared to the spot size. As noted above in one embodiment there is only one via under the spot, and hence the one via must be carefully registered to the spot. In embodiments with multiple vias (say 20 vias under the spot), the measurement is made much more rapidly, as no registration is required and the noise due to overlap between the spot and the number of vias under the spot is small.

A reflectance measurement, of the type described above, is used to detect an irregularity in a pattern of a dielectric layer (during act 204 of FIG. 2) by comparison in some embodiments with a predetermined limit that is set based on past experience with defect-free patterns. Alternatively, a defect in a patterned dielectric layer is detected in some embodiments by finding an aperiodic signal response in a scan in space across a periodic structure of the type shown in FIGS. 3A-3B.

Such a change in reflectance measurement may also be detected in some embodiments of act 204 (FIG. 2), by comparing a current measurement with a reference measurement (made in a sample wafer that is not a production wafer) from a region that is defect free, e.g. as determined by use of any prior art method such as SEM sectioning. In SEM sectioning, the sample wafer is broken, or a focused ion beam (FIB) is used to cut away material, exposing a side view of the via hole. Then, a scanning electron microscope (SEM) is used to image the via hole.

If in act 204, the measurement is found to be unacceptable, then further processing of the wafer is discontinued (and the wafer is discarded in many embodiments). On the other hand, in some embodiments, when the measurement is unacceptable, act 205 is performed to check if the number of unacceptable measurements exceeds a predetermined limit (e.g. no more than 2), and if so then the wafer is not processed further (e.g. discarded). Note that instead of being discarded, the wafer may be taken out of production and examined to find the cause of the deviation. If the predetermined limit is not exceeded, then another act 207 is performed. If in act 204, the measurement is found to be acceptable then again act 207 is performed. In act 207, a check is made as to whether there are any more regions in which openings are yet to be evaluated, and if so then act 203 is performed again. If there are no more openings to evaluate, then act 210 is performed, wherein the wafer is processed further, e.g. to inlay a conductive material in the openings, i.e. to continue with the damascene process in the normal manner.

In some embodiments of the type described above, act 203 is performed immediately after formation of holes 302A-302N in which case underlying conductive layer 301 is exposed unobstructed through holes 302A-302N if no residue is left. If a residue is left—which is to be detected as a process problem—then the metal is not exposed unobstructed. If an etch process is used to open holes 302A-302N, then the reflectance measurement performed after the etch process (and optionally after a clean step discussed below) is also referred to as a "post-etch" measurement.

In certain other embodiments of the type illustrated in FIG. 4, act 203 is performed after a liner 401 is deposited or otherwise formed all over wafer 300. Liner 401 may have a thickness Tliner of, for example, 15-30 angstroms if formed by atomic layer deposition (ALD) or by physical vapor deposition (PVD). Note that thickness Tliner may be a few hundred angstroms on the dielectric layer and tens of angstroms in the trenches and via holes, if the layer is formed by PVD. The two components 491 and 492 that form reflected light 490 are similar or identical to the above-described components 391 and 392 except for being less intense (due to lowering of reflectivity by liner 401).

Note that a clean step is often performed, for example, after the etch of holes and trenches (regardless of the order of etching). A purpose of this clean step in some embodiments is to remove residues and/or oxides that may be present on the metal at the bottom of the holes, normally performed after all etching is completed. In addition, in many embodiments, the clean step may remove copper oxide that forms as a result of oxidation of the copper exposed after the etch. The reflectance measurement is performed in several embodiments following the clean step, in a manner analogous to embodiments in which the measurement is performed following the etch, in order to determine if the clean step has properly removed residues and copper oxide.

The clean step may be performed in any manner normally used to remove post-etch residue and/or copper oxide, depending on the etch process which in turn depends on the semiconductor fabrication process being used (e.g. 0.12 μm diameter vias through low-k dielectric located on Cu metal). The clean step may be performed by use of plasma (such as hydrogen plasma) to sputter. The clean step may alternatively performed by putting the wafer in a wet chemical bath containing a mixture of amines, corrosion inhibitors, suspending agents and/or solvents.

In one specific example of the clean step, the following chemical is used: ST-250 available from ATMI, Inc., 617 River Oaks Parkway, San Jose, Calif. 95134, Phone 408.526.9400. The clean step is performed at (or about) the manufacturer-recommended temperature and for (or about) manufacturer-recommended durations, such as 60° C. for 30 minutes. For more information on how such a clean step may be performed, see the article entitled "Effect of Etching Process Deviations and Photoresist Stripping on Contact Yield of Copper Dual Damascene Metallization" by Ahila Krishnamoorthy, Vladimir Bliznetsov, Hui Leng Tay, and Bo Yu Journal of The Electrochemical Society—December 2002—Volume 149, Issue 12, pp. G656-G660, which is incorporated by reference herein in its entirety.

Figure 1B:
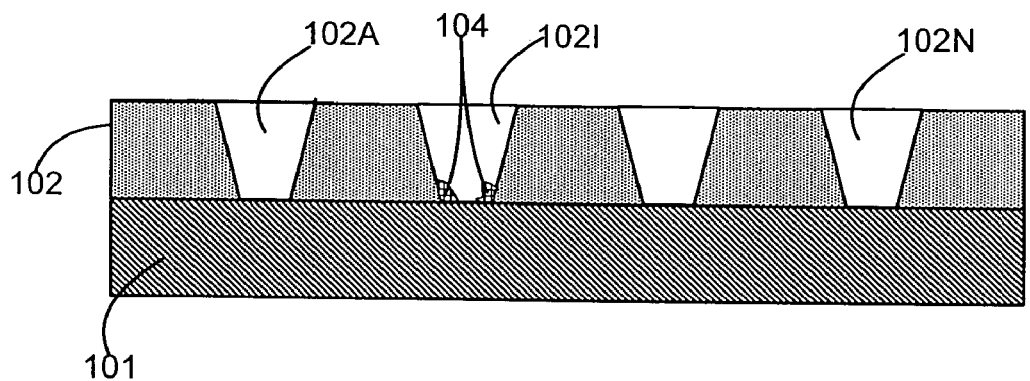
Figure 1C:
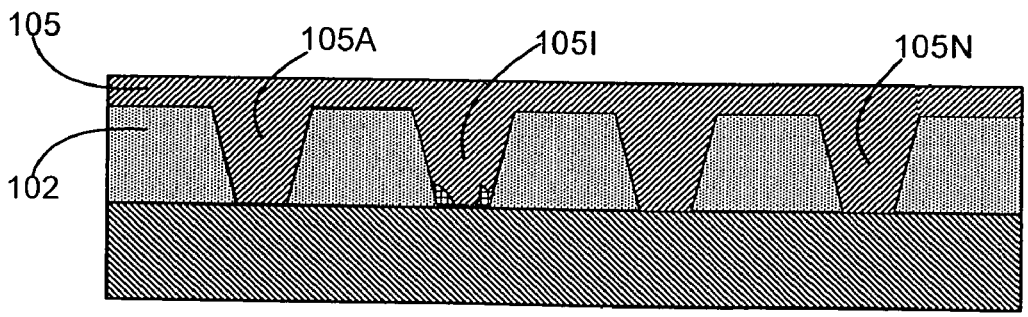

A chemical that is used in the clean step may contain, for example, one or more of the following: N-methyl pyrrolidinone (NMP), hydroxyl amine, ethanol amine, 2-ethoxy 2-ethanol amine, diethylene glycol monobutyl ether. Note that ST-250 described above does not contain any hydroxylamines. Note also that the specific details of a clean step are different in different embodiments, although in many embodiments an etch step and a clean step are performed (in this order), prior to reflectance measurement as described herein. Note also that a clean step of the type described above may use any number of tools and/or tanks (also called "baths"), depending on the embodiment Examples of a liner layer 401 are (1) a barrier layer that is normally used to prevent diffusion of the conductive material into the dielectric layer, (2) a seed layer that is normally used to electroplate a conductive material in future, and (3) a capping layer to retard copper electromigration, e.g. a cobalt-tungsten-phosphide layer also called "CoWP" layer (CoWP is deposited only on the copper using an electroless process. Note that a capping layer, if present, is normally formed prior to a barrier/seed layer. An embodiment where a reflectance measurement that is performed after deposition of barrier/seed layer is also referred to as "post-b/s" measurement. Note that the post-etch and post-b/s measurements are performed before formation and polishing of an overlying metal layer (as shown in FIG. 1C which shows electrodeposited metal before polishing). Reflectance measurements performed after polishing the metal layer are also referred to as "post-polish" measurements.

In the just-described post-b/s measurements, these embodiments have a liner 401, and the acts illustrated in FIG. 2 are preformed as described above, except that the conductive layer 301 is not directly exposed at the bottom of the openings, because conductive layer 301 is covered by liner 401. Note that in such embodiments, a predetermined limit (if used) is different from a corresponding predetermined limit for embodiments that don't have a liner, because presence of the liner changes both via-hole component 392 that is reflected from via holes, and the dielectric component 391 reflected from the dielectric.

In some embodiments, a number of reflectance measurements are made successively one after another in overlapping regions 503A-503P (FIG. 5) in a series of hops across a pattern in space in the dielectric layer (e.g. along the length of a set of vias). In another embodiment, a single reflectance measurement is made in only one region 503I of each die, although covering a number of vias in that single measurement. In such an embodiment, the single measurement of one die may be compared with a corresponding measurement of another die (either in the same wafer or in a reference wafer depending on the embodiment). In still other embodiments, during reflectance measurement a single continuous (analog) signal is generated by a photosensitive element during a continuous scan across the patterned dielectric layer. In such embodiments, a defect in the pattern is detected by finding aperiodicity in the signal in space (in the direction of periodicity of the pattern) as noted above, or by detecting a change from a baseline signal in the case where the number of via holes under the spot is sufficient so that the change in signal due to spatial periodicity of the pattern is small (say <10%).

Figure 6A:
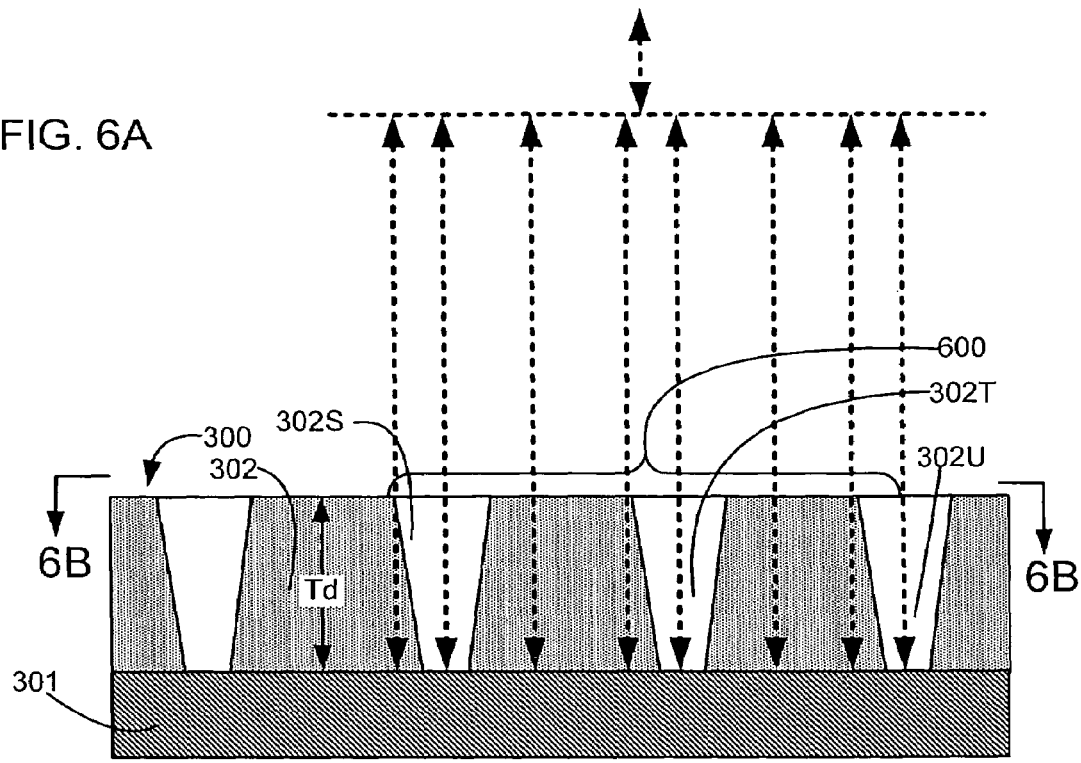
FIGS. 6A and 6B illustrate, in a cross-sectional side view and a plan view respectively, measurement of reflectance in some embodiments, in a region that has a number of via holes through the dielectric layer, prior to formation of trenches.
Figure 6B:
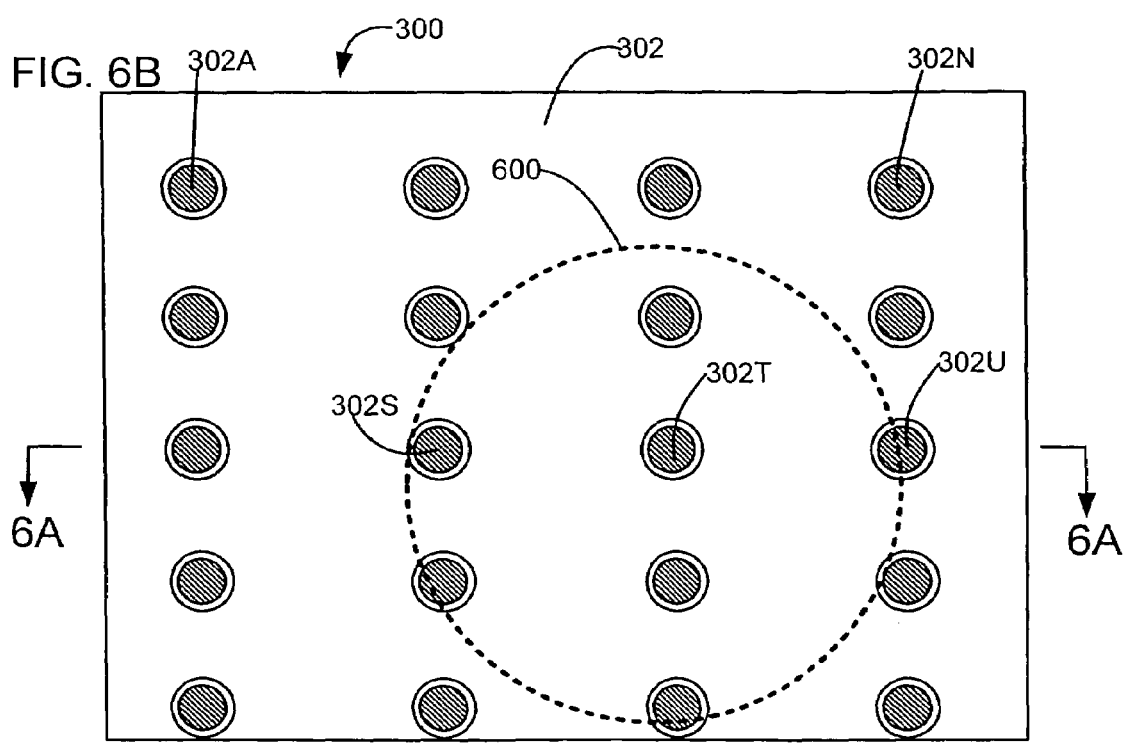

Although in some embodiments, holes 302A-302N are evaluated after formation of trenches 305A-305M, such holes may be evaluated even prior to trench formation as illustrated in FIGS. 6A-6B. Specifically, a reflectance measurement is made in a region 600 that contains a number of via holes, including via holes 302S and 302T and part of hole 302U which holes are holes that pass through the entire depth Td of the dielectric layer 302. Note that in the embodiment illustrated in FIGS. 6A and 6B, a two step etch process is used, wherein the holes are etched first followed by etching of trenches. If the reflectance measurement is unacceptable or if a number of unacceptable reflectance measurements from such a wafer exceed the predetermined limit, then the wafer is not further processed as per act 206 in FIG. 2, without even forming trenches. Hence, in such embodiments, trenches 305A-305M are formed only in wafers that are further processed as per act 210.

Certain specific embodiments that illustrate the invention in greater detail are now described in reference to FIGS. 7A-7D. Specifically, certain embodiments form via holes and trenches in a dielectric layer (in any order relative to one another), as per act 701. Thereafter, reflectance measurements of the type described above are performed by use of two beams: namely a heating beam and a probe beam. As noted above, the heating beam may be selected to have a wavelength in a predetermined band in which the underlying conductive layer 301 (FIG. 3B) is highly reflective (e.g. more than 60% reflective).

Specifically, a "relaxation region" per Drude's model is located between a Hagen-Rubens region and a UV transparent region, and this relaxation region is used to select an appropriate wavelength for the heating beam in some embodiments. Drude defines the "relaxation region" as $1/\tau \ll \omega \ll \omega_p$, with $\tau$ being the mean collision time of electrons in the conductive material, $\omega$ being proportional to the inverse of the wavelength and $\omega_p$ being the plasma frequency of free electron gas in the conductive material. See J. M. Ziman, "Principles of the Theory of Solids, Second Edition, Cambridge University Press, 1972, pages 280-281, which is incorporated by reference herein in its entirety. Note that most embodiments in accordance with the invention can operate in either the Hagen-Rubens or relaxation regions; in both regions the reflectance is high compared to absorption. Specifically, the transition relevant to the invention happens at the plasma frequency $\omega_p$; for frequencies higher than $\omega_p$ (i.e. heating beams of shorter wavelengths), the reflectance drops substantially and for this reason a beam with frequency $\omega \ll \omega_p$ is used in most embodiments as the heating beam.

In some embodiments, an unexpected result is obtained, for example in the case where the underlying conductive layer 301 is formed of copper, and light 380 is preselected to be of wavelength 830 nm (in this example) because the reflectance of copper at this wavelength is very high at 97%, which is an order of magnitude higher than 3% absorptance. Note that certain embodiments that use Drude's model may select any wavelength greater than 620 nm when evaluating structures that contain copper in layer 301, because copper undergoes a sharp transition in reflectance (e.g. from 50% reflective to over 80% reflective across a wavelength range of 517 nm to 620 nm). A heating beam of wavelength sufficiently large to obtain very high reflectance is used in several embodiments to evaluate conductive structures that contain in layer 301 the materials as shown below.

| MINIMUM WAVELENGTH | MATERIAL |
|---|---|
| 620 nm | Copper |
| 120 nm | Aluminum |
| 330 nm | Silver |

Use of a heating beam whose reflectance is at least two times (and in many embodiments one or more order(s) of magnitude) larger than absorptance provides a heightened sensitivity to the surface condition of layer 301, and to coatings or residues on layer 301 that change the reflectance in an amount normally considered insignificant. If 30 milliwatts of light is incident, then only 3% (i.e. 1 milliwatt) of the incident light is absorbed, a coating that reduces the reflectance by 0.33% increases the absorption by 10%. This change is in effect a gain of over 30×, and provides an unexpectedly high sensitivity to small changes in reflectance.

Therefore, a 830 nm wavelength laser (e.g. aluminum-gallium-arsenide laser) is used in some embodiments to generate a heating beam as described herein, to generate a substantial and readily detectable change in amount of applied heat, and hence a corresponding change in the measured signal. Depending on the application, a small number of embodiments do not have the above-described heightened sensitivity, due to use of light of reflectance that is not several times larger, but still larger than absorptance, e.g. by use of an argon laser (of 532 nm wavelength) for which copper has a reflectance of 62% (which is greater than the absorptance of 38%). Other embodiments operate at very high reflectance, e.g. by use of an indium-gallium-arsenide laser (of 1 μm wavelength). Note that some embodiments may even use a heating laser of 2 μm wavelength or 3 μm wavelength, because copper is highly reflective at these wavelengths.

Figure 7B:
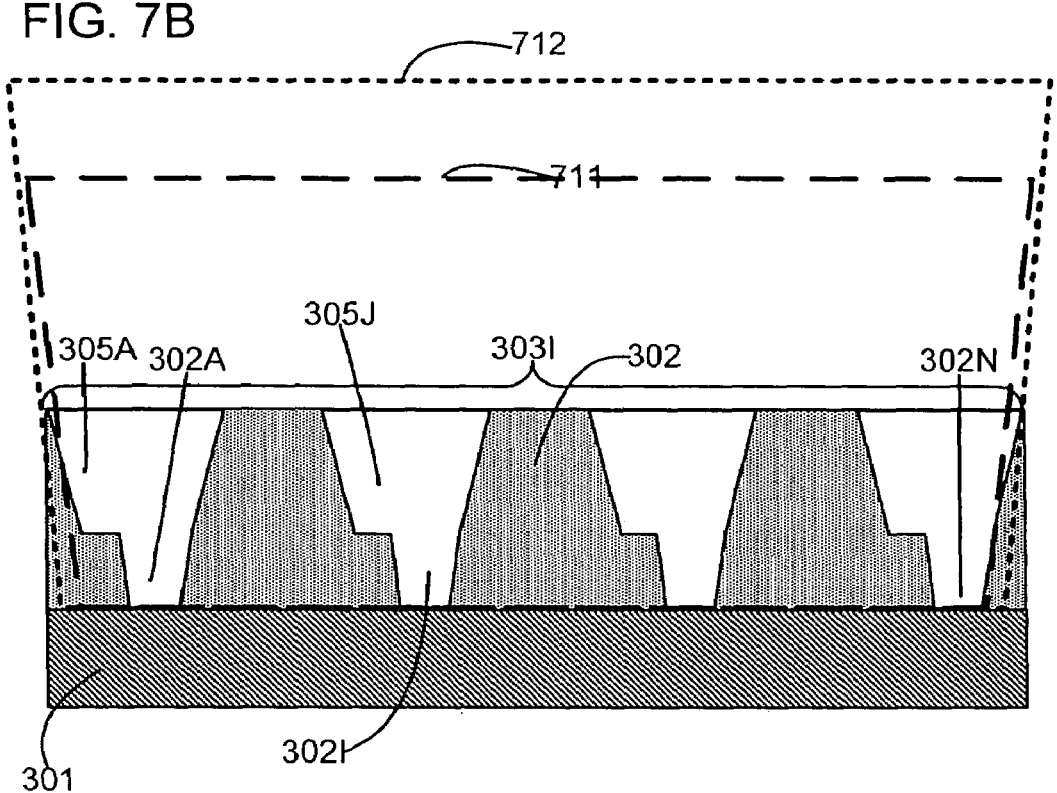
FIG. 7B illustrates, in a cross-sectional side view, use of a heating beam and a probe beam in some embodiments, to measure reflectance of a region 303I of via holes 302A-302N.

In some embodiments, a region 303I of dielectric layer 303, which has at least hole 302I, is illuminated with two beams, namely a heating beam 711 and a probe beam 712 (see FIG. 7B). Heating beam 711 can be any kind of beam, e.g. an infrared beam or an electron beam or an ion beam. In one embodiment, the power of heating beam 711 is modulated at a predetermined frequency, although in other embodiments the modulation may encompass multiple frequencies or patterns in time, such as a chirp or a phase code. Hence, the temperature of underlying conductive layer 301 in region 303I changes, at the frequency of modulation. The modulation frequency is selected in some embodiments to be sufficiently low to ensure that at least a majority of heat is transferred out of region 303I not by a thermal wave but by thermal diffusion.

The power of a portion of probe beam 712 that reflects from illuminated region 303I is measured as per act 703

(FIG. 7A) at the frequency of modulation of heating beam 711. Reflectance of region 303I (or of a region at a fixed distance from region 303I) may be measured in act 703 in any manner, e.g. by use of a photosensitive element to measure energy of probe beam 712 that is reflected from the region under evaluation. Depending on the embodiment, a photosensitive element (or an array of such elements in case of a thermal imager) of the type used in act 703 may be tunable to a wavelength (or a wavelength range) of interest (e.g. 3-5 micrometer). Instead of tuning, a filter or other device may be used to limit radiation incident on the photosensitive element.

In act 704, a check is made as to whether the measurement exceeds a predetermined value, to decide on acceptability of the illuminated via hole(s) for forming via(s). Measurements in multiple regions in the same wafer 300 may be compared to one another in act 704. If a measurement is not acceptable, acts 705 and 706 are performed in a manner similar or identical to acts 205 and 206 (discussed above). If yes, act 707 is performed in a manner similar or identical to acts 207 (also discussed above). In act 707, if all via holes have been evaluated and found acceptable, then a barrier layer and/or a seed layer is formed (as per acts 708 and 709). One or more such liner layer(s) may be formed by atomic layer deposition or by sputtering. If such layers are already formed or if they are not to be formed then act 710 is performed in a manner similar or identical to act 210 (described above).

Figure 7D:
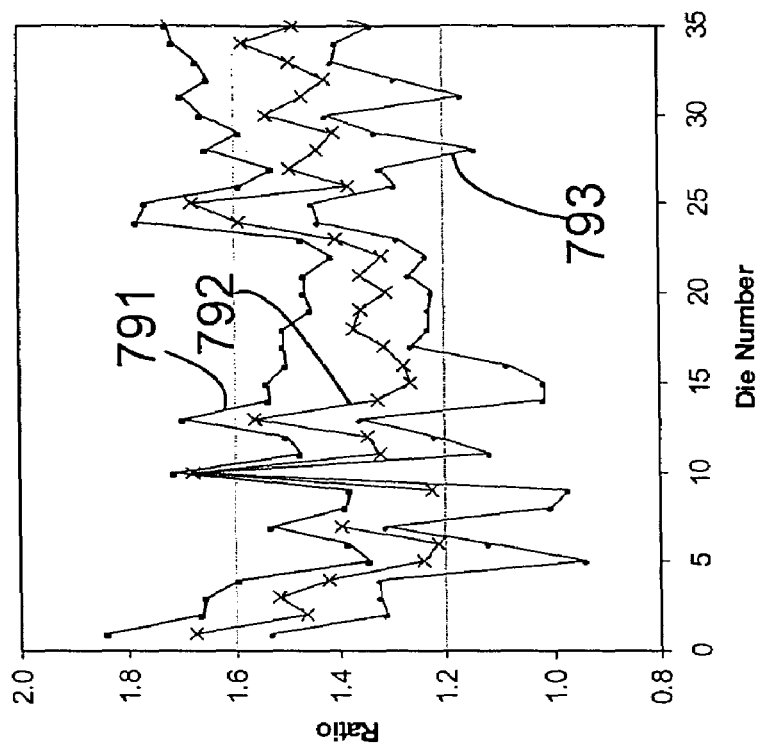
FIGS. 7C and 7D illustrate, in graphs, absolute measurements and relative measurements respectively, of reflectance in regions of the type illustrated in FIG. 7B with about 25 via holes in each spot in a structure having a continuous metal layer.
Figure 7C:
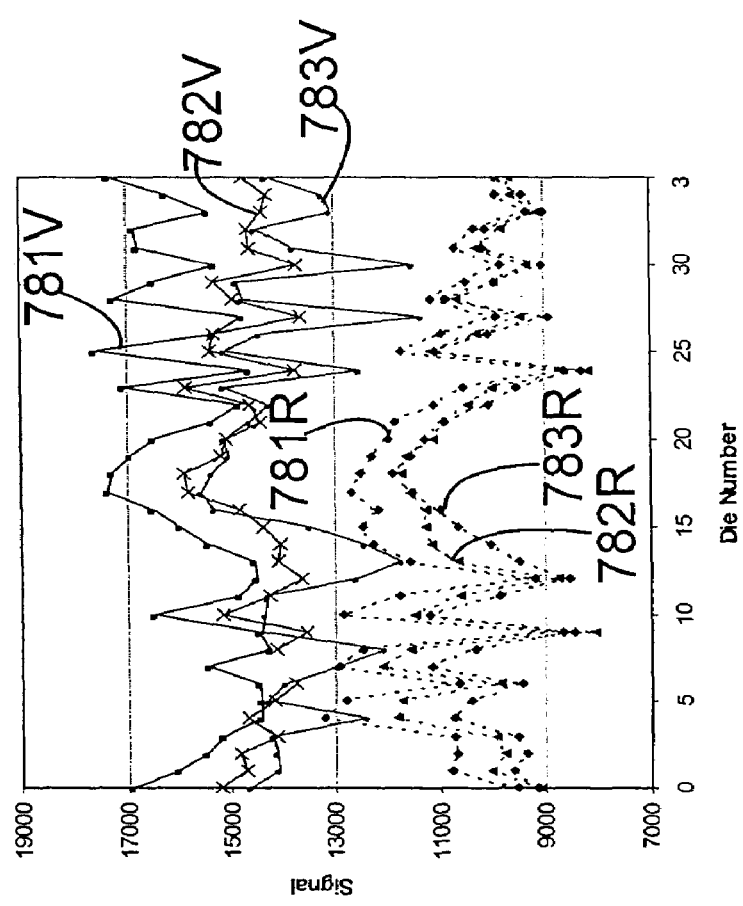

Measurements of the type performed in act 703 are shown in a graph in FIG. 7C. The measurements in FIG. 7C were made for a dense via structure in wafer 300, wherein via holes were 0.14 μm in diameter, with centers separated from one another by 0.3 μm pitch, and the underlying conductive line had 0.14 μm width. This structure exposes almost ⅓rd of the area of underlying layer 301. In this example, if the via hole clearing process was inadequate and left a residue at the bottom that changed reflectivity from 97% to 96%, then the light absorption increases by 11% (33% increase in absorption in the exposed portion of the line, which is ⅓rd of its area). This results in an 11% increase in temperature of the conductive line in layer 301, a change that is readily detected.

In FIG. 7C, graphs 781R-783R are for reference measurements from structures without via holes, and graphs 781V-783V are for measurements from structures with via holes. Specifically, graph 781V is for etching the holes for 100% of time in a best known method, whereas graphs 782V and 783V are respectively for 60% of the time and 40% of the time respectively. Note that the large die-to-die variation seen in FIG. 7C is due to both the via hole variation and the across-wafer thickness variation of the underlying conductive layer 301.

The measurements of graphs 781V-783V shown in FIG. 7C when divided by corresponding normalization measurements of graphs 781R-783R from identical (or similar) regions that are devoid of via holes, are shown by graphs 791-793 in FIG. 7D. In the just-described example, a value of 1.7 is preselected as the limit on such a ratio, to be used in deciding acceptability of the measurement in act 704. In this example, measurements from dies 10, 12, 24 and 25 are found unacceptable in act 704. Therefore, this wafer is not processed further, e.g. inlay of copper into holes and trenches is avoided thus saving the cost of such a step on a defective wafer. In the example illustrated in FIGS. 7C and 7D, the dimensions of the via holes were: 0.14 μm diameter, 0.3 μm deep, and the dimensions of the illuminated region were 2.5 μm diameter, and the probe beam wavelength was 980 nm, and heating beam wavelength was 830 nm.

A processing unit 810 (FIG. 8A) is operated in accordance with the invention to create integrated circuit (abbreviated as "IC") dice by processing a wafer 804 to form a patterned wafer 805, measuring the reflectance of one or more holes in patterned wafer 805, and adjusting the processing in real time if necessary. Specifically, unit 810 includes a dielectric formation apparatus 811 that forms on wafer 804 a layer of dielectric material to create wafer 803 that is in turn is processed by dielectric patterning apparatus 812 that etches patterns into the dielectric film to form one or more holes in wafer 805. Patterning apparatus 812 includes a photolithography system to form a pattern in a photoresist mask, an etcher to etch the ILD through the photoresist mask pattern, and a stripper to remove the photoresist after patterning.

Unit 810 also includes a measurement apparatus 813 that measures the reflectance of one or more regions on patterned dielectric in wafer 805. If the measurement falls outside of the specifications for wafer 803 or 804, a process parameter can be adjusted by measurement apparatus 813. One embodiment of apparatus 813 includes an optional programmed computer 813C that drives an active signal on line 814 that is coupled to dielectric patterning apparatus 812, or on line 815 that is coupled to dielectric formation apparatus 811, or both, depending on the measurement. A change in the process parameter can be determined automatically by software in programmed computer 813C, or can be entered by a human operator.

Measurement apparatus 813 determines, between acts of fabricating unpatterned substrate 804 or patterned substrate 805 (FIG. 8B), a measure of the electrical resistance by use of two coincident beams 801 and 802 of electromagnetic radiation (such as laser beams). A first beam (also called "heating beam") 801 has a power (also called "heating power") that is modulated at a predetermined frequency. A second beam (also called "probe beam") 802 is continuous. First beam 801 is incident on and heats a region around a hole in substrate 803, 804 or 805 (see FIG. 8A) to a temperature T, and second beam 802 is reflected by the heated region at the modulation frequency of first beam 801, because temperature T is modulated at the modulation frequency of first beam 801.

The predetermined frequency of modulation of first beam 801 is selected to be sufficiently small to ensure that a majority (i.e. greater than 50%) of heat generated by first beam 801 flows by thermal diffusion out of the heated region (e.g. along the length L of line 111 in substrate 105). In one embodiment, the predetermined frequency is selected to cause substantially all (e.g. greater than 90%) of heat generated by first beam 801 in a conductive region 111R at the bottom of a via hole to be transferred to adjacent conductive regions 111S and 111T by diffusion.

Figure 9A:
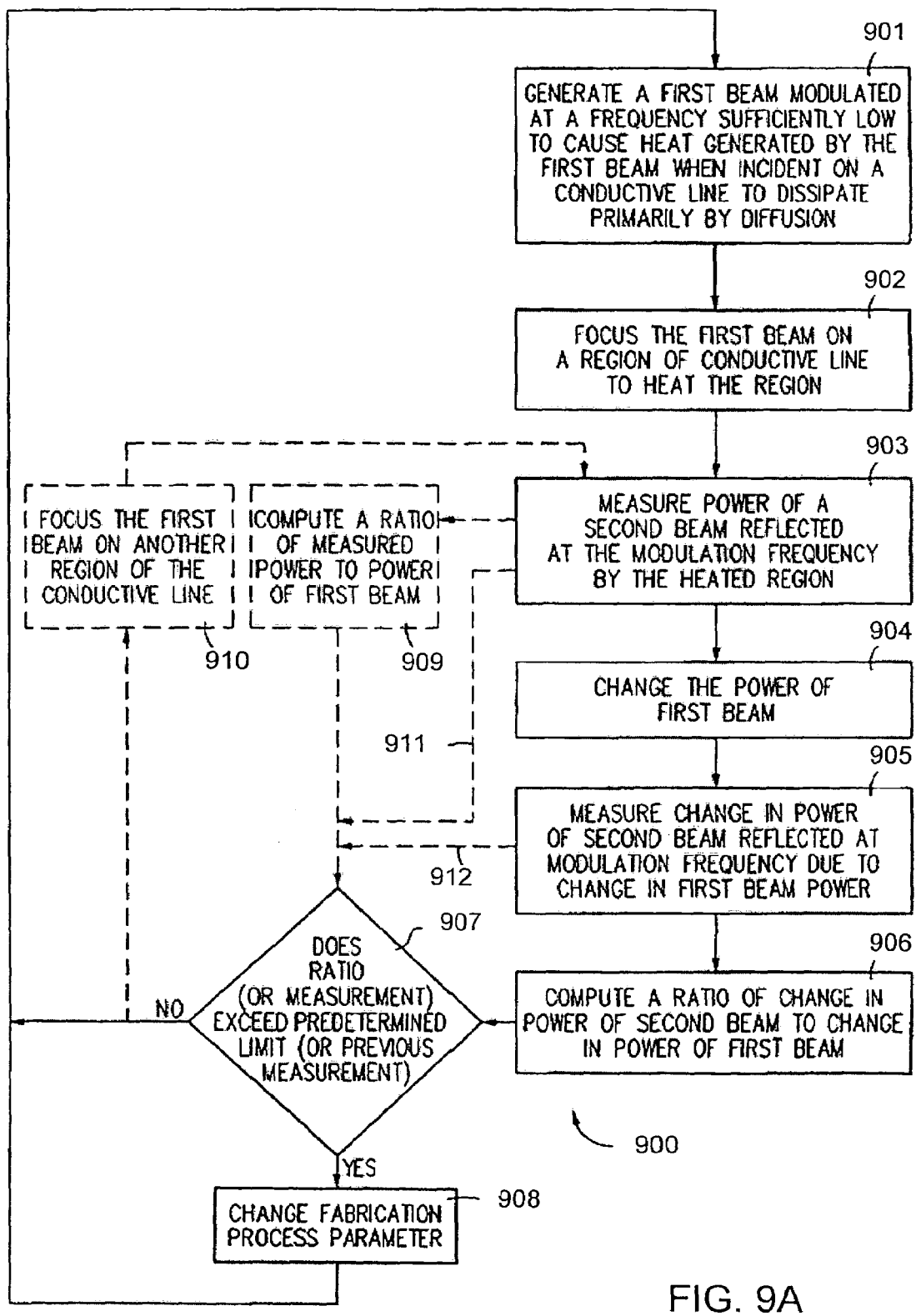
FIG. 9A illustrates, in a flow diagram, a method for using the two beams of FIG. 7B to measure a change in reflectance of a region, and use of the measurement to control the processing of wafers by the dielectric formation apparatus and dielectric etching apparatus in FIG. 8A.

Such a diffusive heat transfer allows the use of a diffusion equation solution to relate electrical and thermal conductivity in a measurement method 900 (FIG. 9A). Therefore, the predetermined frequency is selected to be lower than a maximum frequency beyond which the effects of a thermal wave become noticeable. The maximum frequency is inversely related to a dimension of conductive region 111R (e.g. the length L) of line 111. In one embodiment, length L is approximately 100 microns, and the maximum frequency is 1430 Hz for copper lines, and 1080 Hz for aluminum lines. In another embodiment the frequency is 2 KHz and length L is 10 μm so that maximum frequencies are 14,300 and 10,800 Hz for copper and aluminum respectively. Note that waveforms that have frequency components within this range may also be used, for example, a chirp spanning a frequency range from 10 to 14 KHz.

Note that the following discussion makes a specific reference to a conductive line 111, although a similar analysis in applicable to a two-dimensional portion of a conductive layer 111. Moreover, although the following description refers to a wafer of silicon (such as wafer 803, 804, or 805) that is processed into integrated circuit dice, the description is equally applicable to any substrate that supports a conductive layer, and other examples of such a substrate include a glass plate that is processed to form a liquid crystal display and a resin core that is processed to form a printed circuit board. For convenience, the same reference numerals are used for a wafer and a substrate.

The diffusion of heat from conductive region 111R that is directly heated by light which travels through a hole in dielectric layer 119 creates a temperature profile 150 (FIG. 8C) in conductive line 111, with a hottest point C (having a peak temperature Tp) located at the center of conductive region 111R under the following assumption. In one example, conductive line 111 is supported on a dielectric layer 112 (FIG. 8B) of a wafer 805 having a thermal conductivity Ki that is almost two orders of magnitude lower than the thermal conductivity Km of conductive line 111. Note that such a large difference in thermal conductivities is not required for some embodiments. Instead, diffusion equation solution holds as long as the thermal conductivity Ki of dielectric layer 112 is smaller than the thermal conductivity Km of line 111.

Peak temperature Tp (FIG. 8C) is a function of thermal conductivity Km and the cross-sectional area W×hm of conductive line 111, wherein W is width and hm is height of line 111. As the electrical and thermal conductivities are related, peak temperature Tp indicates (as discussed more completely below), per unit length, conductive line 111's electrical resistance.

Temperature profile 150 has substantially the same "bell" shape (FIG. 8B) over length L at any time during a cycle at the predetermined frequency. Therefore, temperature T is modulated without forming a wave in space (in a manner analogous to direct current ("DC")) during the cycle. Temperature T is modulated only to increase the accuracy in measurement, specifically the signal-to-noise ratio by use of synchronous detection of a portion of probe beam 802 reflected by region 111R. Moreover, the predetermined frequency can be arbitrarily low, limited only by the minimum throughput required of the fabrication process.

As noted above, in some embodiments, the measurement is made with via holes penetrating to short metal links. These links are conductive lines that may be on the order of or smaller than the spot size in length. For example, a link may be 0.4 μm long, 0.14 μm wide, and 0.3 um thick. In this case, the link rises to a uniform temperature, as there is negligible heat flow out of the link because the link is surrounded by dielectric material with low thermal conductivity.

Figure 7E:
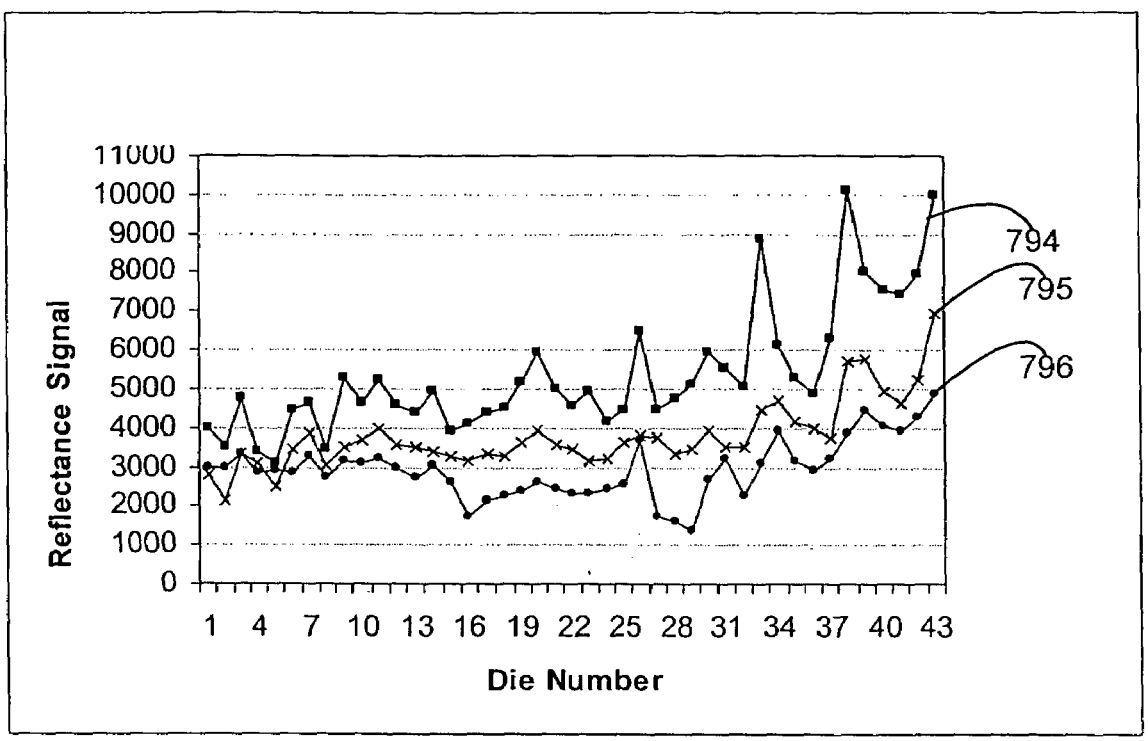
FIGS. 7E and 7F illustrate, in graphs, reflectance measurements in a structure having isolated metal elements underneath a patterned dielectric layer, in regions across the entire wafer.
Figure 7F:
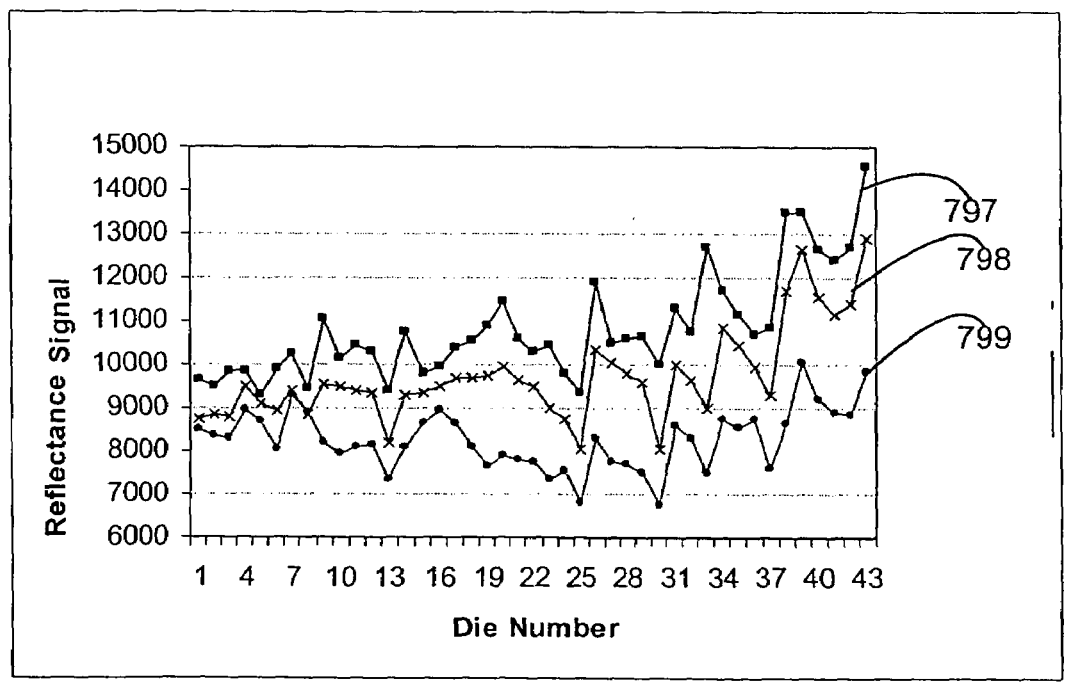

Some embodiments use the BX-10 measurement tool available from Applied Materials, Inc. of Santa Clara, Calif. to obtain reflectance measurements of the type illustrated in FIGS. 7E and 7F. Specifically, FIGS. 7E and 7F show reflectance measurements (obtained by BX-10) on structures containing metal links located underneath a dielectric layer that are approximately 0.5 μm long with via holes 0.14 μm in diameter. The links are 0.14 μm wide and spaced laterally 0.32 μm for the data in FIG. 7E and 0.36 μm for the data in FIG. 7F. Curves 794, 795 and 796 of FIG. 7E show via hole etch conditions corresponding to the normal process time, 60% of the normal process time, and 40% of the normal process time.

Because the links float in temperature, the reflectance measurement is less sensitive to local variation in dielectric properties, and normalization or correction is not needed to distinguish to process conditions related to the vias from process conditions related to other factors such as dielectric and metal line thickness, as was the case in FIGS. 7C and 7D. Note also that the links in structures being evaluated as shown in FIGS. 7E and 7F are very short, so the frequency of modulation may be correspondingly higher, while continuing to maintain diffusive heat transfer conditions. Whereas approximately 10 KHz was a modulation frequency used in evaluating structures containing conductive lines of length 10 μm, modulation frequencies that are orders of magnitude higher, e.g. around 200 KHz are now used in some embodiments that evaluate structures containing 0.5 μm links, because of the shorter length of the links.

As an example of such embodiments a reference value of 4000 microvolts may be set as a lower limit for determining acceptability of production wafers. Note that curve 794 in FIG. 7E is for the best open etch time, and hence only a few measurements (at dies 4 and 5) fall below the reference value, whereas a significant number of measurements on curves 795 and 796 fall below this reference value (thereby causing such wafers to be rejected). Note that similar curves 797-799 in FIG. 7F are for a wafer with a different interconnect structure, and in this case the reference value (for acceptance of production wafers) may be set at 9000.

In one embodiment, a measure of the electrical resistance of line 111 is determined by performing acts 901-906 of a method 900 (FIG. 9A). Specifically, in act 902, heating beam 801 is focused on a region 303I that contains at least one opening as noted above. In act 901 (FIG. 9A), the power of heating beam 801 is modulated at the predetermined frequency. Note that acts 901 and 902 can be performed in reverse order, i.e. act 902 performed first followed by performance of act 901.

Next, the power (also called "reflected power") of probe beam 802 after reflection by region 111R is measured in act 903. Thereafter, in act 904, the power of heating beam 801 (FIG. 8B) is changed, e.g. increased from 1 milliwatt to 5 milliwatts. Next, in act 905 (FIG. 9A), a change in the reflected power in response to the change in power of heating beam 801 is determined. Thereafter, in act 906, a ratio of the change in reflected power to the change in power of heating beam 801 is computed. The ratio indicates reflectance in the heated region. Note that during the just-described operations, the power (also called "probe power") of probe beam 802 that is incident on the heated region remains constant in this embodiment. The ratio may itself be compared (in act 907) with a predetermined limit to check if line 111 is within specifications and if so, return to act 901 (for another wafer).

In most cases there is a linear relationship between the measured signal and the power reflected. In such cases, the condition of zero heating power may be used as one of the powers of the beam, and only a single power measurement is required, thereby to make the evaluation faster than if multiple measurements are made. The ratio is now just the signal measured at a fixed heating power. In one implementation, heating beam 801 is focused (in act 910) in another region and the measurement is repeated (in act 903), and the two measurements are compared. Any residue presence or change in diameter of a via changes the steady-state ratio, and is also detected by the just-described comparison. Note that the above-described analysis assumes that there are no irregularities in conductive line 111, e.g. because wafers with such irregularities are assumed to have been discarded prior to formation of the patterned dielectric layer. Note also that although in some embodiments a measurement of the type described above varies linearly as a function of the power of the heating beam, in another embodiment, the response vs. power is non-linear, and hence a reference signal value is set using a calibration based on measurements on reference wafers.

In one implementation, the above-described measurements (either a single measurement or two or more measurements per region) are repeated after focusing (see act 910) heating beam 801 in each of a number of successive regions on conductive line 111. Instead of comparing numerical measurements, a change in the steady state ratio can be detected by plotting a graph of the steady state ratio as a function of distance. Therefore, the event of a change in the steady-state ratio (e.g. exceeding a predetermined limit) provides an indication that the fabrication process has changed, and that via holes are no longer within specification.

In response to the indication, an operator or an appropriately programmed computer changes a process parameter that controls the fabrication of line 111 (see act 908 in) FIG. 9A and that changes the process to return via holes being formed in the next wafer to within the specification. For example, the operator identifies an under-etch in dielectric patterning apparatus 812 (FIG. 8A) that affects a via formed in wafer 803, and changes a parameter related to the source.

In a related embodiment, the standard deviation of reflectance measurement along a line is computed. For instance, 100 sites are measured at 2 µm spacing along a straight line, and the standard deviation of the 100 measured signals is computed (and optionally reported). If the patterning process is in control, the standard deviation will be small and all measurements fall within one standard deviation (also called "sigma"). Depending on the embodiment, other limits may be set, such as (1) if more than five measurements that exceed one sigma then the substrate is not further processed (e.g. discarded) and/or (2) if more than two measurements exceed two sigma then the substrate is not further processed and/or (3) if more than one measurement exceeds three sigma then the substrate is not further processed. An out-of-control process may, for example, leave a "spotty" pattern, that is, not uniform spatially, residue, which manifests itself as an increased standard deviation of the signal.

A steady-state ratio as described above is measured at a single spot (e.g. in region 111R), allowing the measurement (of the value of reflected power) to be made in a more compact area (e.g. a region of length 1 micron) than possible by a method that requires two connected locations (each displaced from the other), e.g. as disclosed in U.S. Pat. No. 5,228,776. In the just-described example, since only the power of beam 801 that is incident on line 111 heats the line, width W (FIG. 1B) of line 111 can be smaller than the diameter of beam 801 (that may have a minimum size larger than line width W). The temperature of a region 111R (of length equal to the diameter of beam 801) in line 111 that is heated under diffusive conditions as described herein is a function of the thermal properties of an extended length L (typically several tens of microns) of line 111 about the heated region 111R.

In the prior art (e.g. U.S. Pat. No. 5,228,776), the heat propagates away from a heated region in a thermal wave, and the temperature at the heated region is not a direct function of the physical properties of the conductive line at a distance. This is because a thermal wave at any point is the sum of heat from an outgoing wave and heat from waves reflected from one or more regions in the line where the metal properties have changed. This sum is difficult to quantify in the prior art, because the reflective properties of defects may not be known in advance. Note that such a method would not even be feasible for isolated links as there is no thermal conductive path.

In contrast, during diffusive heat transfer, the heat at any point is affected in a quantifiable manner by the reflective obstructive (that is, blocking or constricting the flow of heat or, in the case of a short, expanding the heat flow path) properties of holes that are illuminated. Also, method 900 provides an unexpected result, specifically the value of reflected power as measured by method 900 is unaffected by the presence of non-flat surfaces (that cause problems in the prior art, e.g. U.S. Pat. No. 5,228,776) because a reflectance measurement as described herein is independent of the small angular deflection that is caused by periodic undulation of a surface by passage of a thermal wave.

In one example, apparatus 813 operates heating beam 801 at 0.01 watts and at 0.02 watts and obtains intensity measurements for these two powers as follows: probe beam has an incident power on heated region 111R of 1.1 milliwatts, and (1) a modulated component of reflected power of 0.55 microwatts, thereby yielding $\Delta R=(0.55/1.1)\times 10-3=0.5\times 10-3$; and (2) a modulated component of the reflected power of 1.1 microwatts, thereby yielding $\Delta R=(1.1/1.1)\times 10-3=1\times 10-3$. Therefore, the slope is $\Delta R/\Delta P=(1.0-0.5)/(0.02-0.01)\times 10-3=0.05$. The value of 0.05 of the slope is thereafter used with a constant (as described below in reference to equation 20) to obtain a reference value from one or more known-to-be good wafer(s), which is then used to evaluate wafers under fabrication. Note that instead of using two measurements, a single measurement (e.g. at 0.01 watts of heating beam power) can be used, e.g. by computing $\Delta R/\Delta P$ as $(0.5/0.01)\times 10-3=0.05$ assuming that the $\Delta R$ is zero when $\Delta P$ is zero.

In an alternative embodiment, instead of performing acts 904-906, another ratio is computed in act 909, directly after act 903, based on the fact that a modulated component of the reflected power is zero when the power heating beam 801 is zero. Specifically, a ratio of a modulated component of the reflected power to the power of heating beam 801 is computed, and used as a measure, per unit length, of the electrical resistance of conductive line 111 in act 907. Furthermore, instead of computing the ratio, the reflected power can also be used directly (by going from act 903 directly to act 907 as per branch 911 or by going from act 905 directly to act 907 as per branch 912) as a measurement parameter, if power of heating beam 801 is constant for each of a number of measurements for the corresponding regions e.g. regions 111R-111T.

In some embodiments, the reflected power is normalized to the power of the probing beam, in order to remove the effect of surface reflectance variation. One embodiment does not normalize the probe beam power to the heating beam power, although this is done in other embodiments.

Use of steady-state conditions as described herein eliminates the need for a generation beam having the high modulation frequency required by U.S. Pat. No. 5,228,776 to set up a thermal wave. Specifically, the above-described method eliminates the need to generate a beam modulated at a frequency in the range of 1 MHz to 100 MHz, and instead requires a beam modulated at a frequency that is several orders of magnitude smaller, e.g. in the range of 0.01 KHz to 10 KHz, thereby eliminating the thermal wave.

Figure 9B:
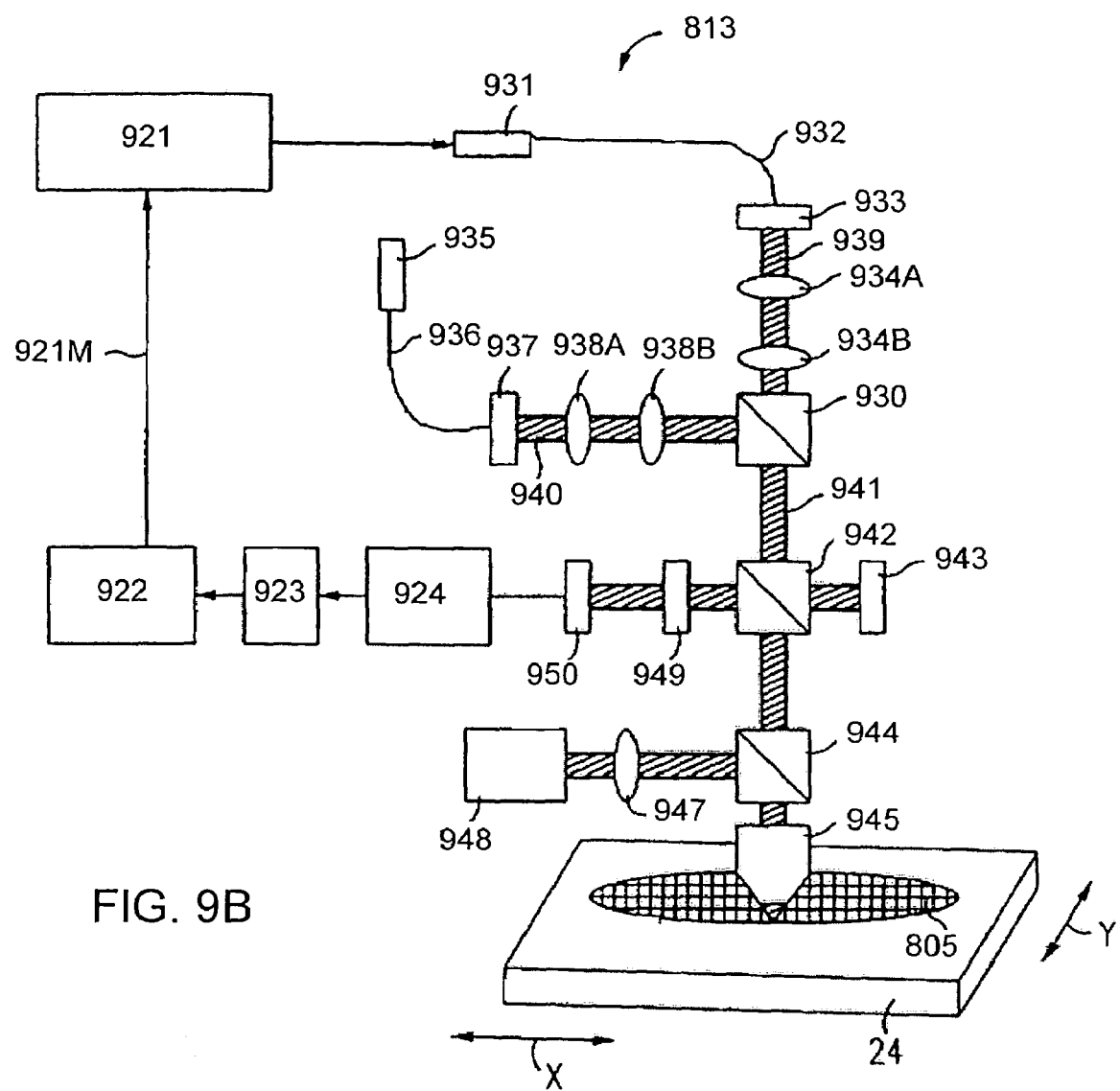
FIG. 9B illustrates, in a block diagram, a measurement apparatus that performs the method illustrated in FIG. 9A.
Figure 10:
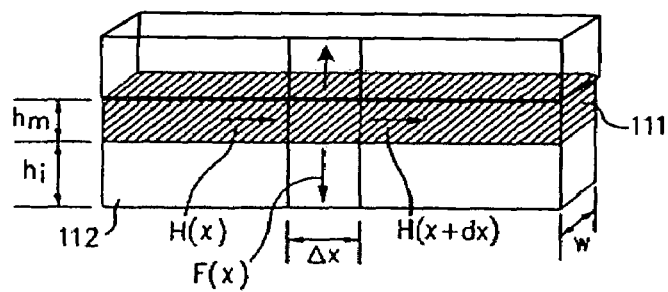
FIG. 10 illustrates the transfer of heat through a portion 111X of a conductive layer and into the surrounding dielectric layers by diffusion under steady state conditions.

Acts 901-906 of method 200 can be performed by use of a measurement apparatus 813 (FIG. 9B) having two lasers that create the two beams 939 and 940. Specifically, apparatus 813 includes a source 931 for creating a beam 939 of electromagnetic radiation at a predetermined wavelength, such as a laser for infrared light and ultraviolet light and sources of X-rays, gamma rays, or radiation in the microwave or radio frequencies. In a preferred embodiment, laser 931 is a AlGaAs diode laser that emits electromagnetic radiation of wavelength 830 nm.

The electromagnetic radiation created by laser 931 is transmitted through an optical fiber 932 to a collimator 933 that emits heating beam 939. In one implementation, heating beam 939 (FIG. 9B) has a maximum power of, for example, 100 milliwatts. Apparatus 813 also includes lenses 934A and 934B that adjust the size of beam 939 to fill the aperture of an objective lens 945 also included in apparatus 813.

Apparatus 813 further includes a second laser 935 that creates a beam 940 of electromagnetic radiation used to measure a change in reflectance of heated region 303I (FIG. 8B) in response to change in power of heating beam 939. In one implementation, laser 935 is an InGaAs diode laser that emits electromagnetic radiation of wavelength 980 nm. The electromagnetic radiation created by laser 935 is transferred by an optical fiber 936 to another collimator 937 also included in apparatus 813. Collimator 937 emits probe beam 940 having a maximum power of, for example, 70 milliwatts. Therefore, conductive line 111 may be heated by probe beam 940, but this heating is constant, so it is not detected by the lock-in amplifier 922 that is only sensitive to signals at the frequency of modulation of heating laser 931.

Apparatus 813 also includes lenses 938A and 938B that adjust the size of probe beam 940 to fill the aperture of objective lens 935 (described above). Apparatus 813 also includes a dichroic beam splitter 930 that combines heating beam 939 and probe beam 940 to form a combined beam 941. Combined beam 941 passes through beam splitters 942 and 944 that are also included in apparatus 813, to an objective lens 945. Objective lens 945 can be, for example, a 0.9 NA, 100× objective lens available from Nikon of Yokohama, Japan. A portion of combined beam 941 is deflected to a second lens 947 and CCD camera 948. Camera 948 is used to verify the alignment of combined beam 941 with respect to wafer 805. A portion of this deflected beam may also be sent through a pinhole to a photocell in order to provide an autofocus mechanism to ensure that the combined beam 941 is focused on the surface of wafer 805.

Light reflected from wafer 805 passes back through objective lens 935 and through beam splitter 942. Beam splitter 942 sends 50% of the reflected light through a filter 949 to a photodetector 950 such as part number J16-8SP-RO5m-HS from EG&G Judson of Montgomeryville, Pa., USA. Filter 949 is a narrow band filter that removes the reflected portion of heating beam 939 while passing the reflected portion of probe beam 940. Thereafter, photodetector 950 senses the intensity of the reflected portion of probe beam 940, and passes a voltage signal to amplifier 924.

Amplifier 924 converts the voltage signal into a current signal and passes the current signal to a lock-in amplifier 923. Lock-in amplifier 923 includes an oscillator 922 as a frequency source that is used to detect the power of the reflected portion of probe beam 840 modulated at the predetermined frequency. The frequency source in lock-in amplifier 923 also provides a frequency signal on a line 921M to a laser driver 921. Laser driver 921 uses the frequency signal on line 921M to drive laser 931 at the predetermined frequency that is sufficiently low to modulate the amplitude of heating beam 939 to ensure heat transfer by diffusion as described herein. Note that oscillator 922 may modulate laser driver 921 with other waveforms such as, for example, a frequency chirp, as a reason for the modulation is to enable detection of low-level signals with lock-in amplifier 923.

Apparatus 813 also includes a beam splitter 944 that diverts 10% of combined beam 941 to a focusing lens 947 and camera 948. Camera 948 is used to observe beams 801 and 802 (FIG. 8B) on wafer 805, in order to focus combined beam 941 (FIG. 9B) within region 303I on wafer 805.

Figure 8A:
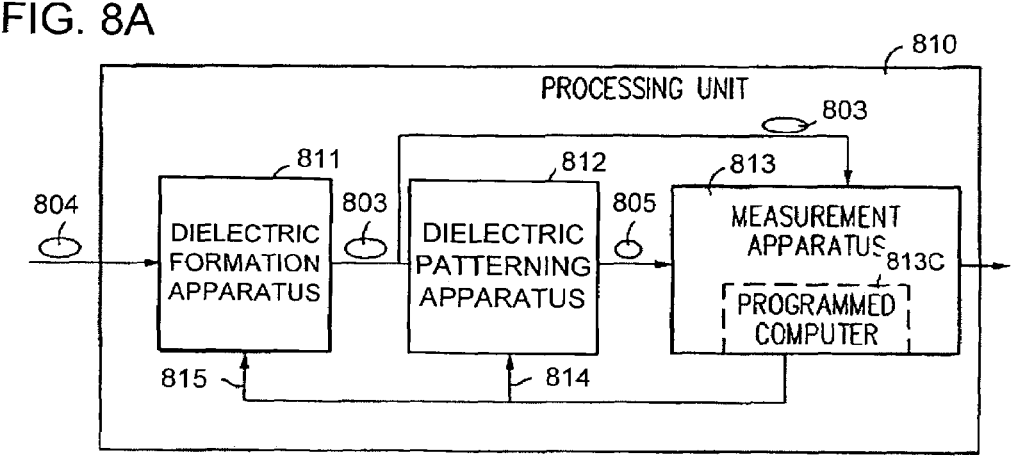
FIG. 8A illustrates, in a block diagram, use of one embodiment of a measurement apparatus of this invention with a dielectric formation apparatus for forming a dielectric layer and a dielectric etching apparatus for patterning the dielectric layer.
Figure 8B:
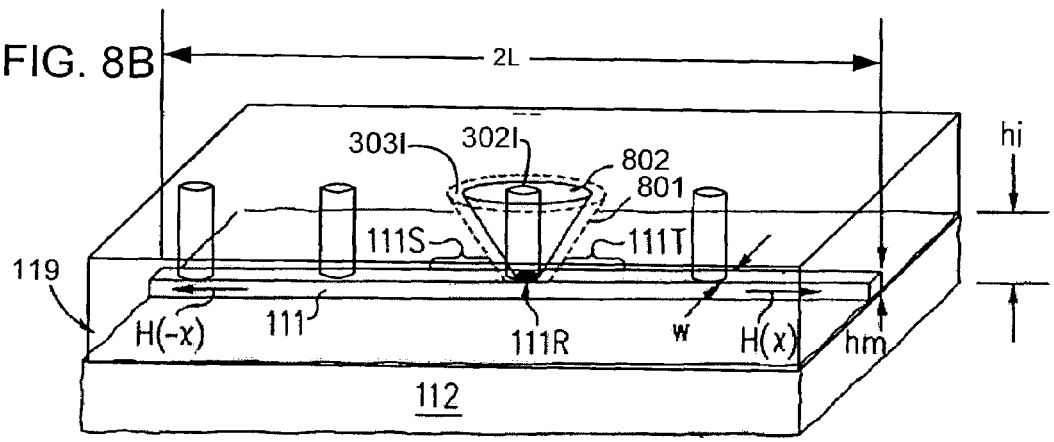
FIG. 8B illustrates, in the apparatus of FIG. 8A, a heating beam focused on a region around a single via hole under steady state conditions while a probe beam is used to measure reflectance of the region in one embodiment of the invention.
Figure 8C:
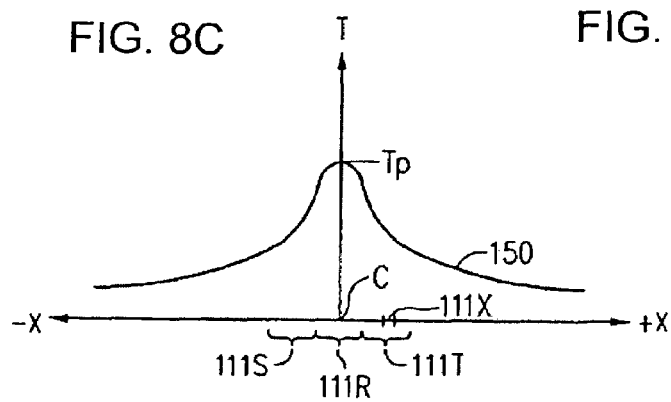
FIG. 8C illustrates, in a graph, the temperature of heated region 111R and of adjacent regions 111S and 111T in the conductive line of FIG. 8B.
Figure 8D:
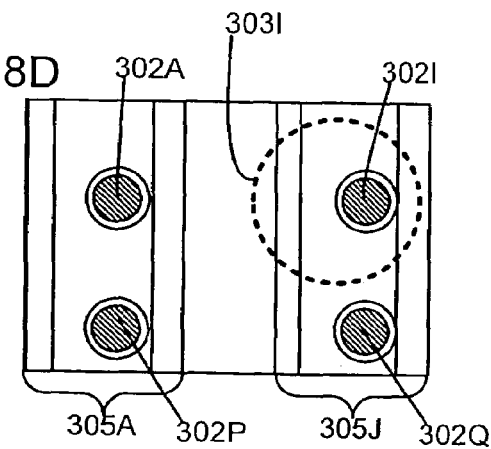
FIG. 8D illustrates, in a plan view, the relationship between spot size and via hole diameter in the embodiment of FIGS. 8A-8D.

Referring to FIGS. 8A-8C, the modulation frequency is inversely related to the distance over which the temperature T decays to, e.g. 10% of the peak temperature Tp. If such a distance (also called "decay distance") is smaller than measurement length L, the maximum frequency can be higher than the just-described maximum frequency. For example, if the decay distance is 20 microns, the maximum frequency is 5985 hz for copper and 5525 hz for aluminum. If the decay distance is 2.5 µm, then the maximum frequency is 48 kHz for copper and 44 kHz for aluminum Temperature profile 150 (FIG. 8C) is determined by solving a static heat equation for region 111R (FIG. 8B), taking into account heat loss into insulation layers 112 and 119. Assume a region 303I around a point 111X of conductive line 111 has a length $\Delta x$, a width w, and a thickness hm. Insulation layer 112 has thickness hi and thermal conductivity Ki, and is assumed to be at the temperature of conductive line 111 at top surface 112T, and at the ambient temperature at the bottom surface 112B.

Heat flux H(x) is primarily along conductive line 111, but a small amount of heat F(x) leaks through insulation layers 112 and 119. By conservation of energy, $H(x)=F(x)+H(x+dx)$, assuming negligible loss (less than 1%) to convection and radiation. Such losses may be included as additional terms added to the loss F(x) due to heat flow into insulators 112 and 119, (especially for convection, which scales as the temperature difference between the ambient and the insulator, as does the loss into the insulator). The diffusive heat flux is given by the derivative of the temperature times the thermal conductivity.

Note that in some embodiments the metal line 111 is a short segment, where the length of the line may be comparable to or smaller than the diameter of heating beam 939 at its focus. In this case, the metal line segment is surrounded by dielectric material which may have a thermal conductivity two orders of magnitude lower than a metal such as copper. The metal line segment in this case is now of constant temperature, and the temperature rises and falls with the modulation frequency. The peak temperature is a function of the ability of the line segment to absorb light from heating beam 939, which will relate to the surface quality, existence of residues, and via hole size.

When two beams are used in embodiments of the type illustrated in FIG. 4, two simultaneous effects occur to indicate the quality of liner layer 401 in the via holes of wafer 300. First, heat conduction occurs to the underlying conductive layer 301 (which may be composed of metal lines). As the liner layer is only partially transmissive, it will absorb light, which will heat the layer. If the liner layer is continuous to the conductive layer, the heat will flow to the conductive layer, which will conduct it away. If the conductive layer is too thin, the conductive layer will heat more, so the temperature of the structure is in indication of the continuity and quality of the liner layer.

Second, as the liner layer is located over the top of the conductive layer 301, the liner layer increases direct absorption of heat into the conductive layer 301. This is because the liner layer is far more absorptive than the conductive layer 301 (typically copper which is reflective). Consequently, the heating of conductive layer 301 is proportional to the thickness of the liner layer at the bottom of the via holes. Such heating is measured by use of the probe beam as discussed above. However, in other cases, the liner may be formed with two separate depositions: a barrier layer made of a material such as TaN, and later on a seed layer made of copper. In this case, when reflectance is measured after the two layers are formed the exposed surface is again copper, and the absorption and heating properties are again dominated by copper.

Numerous modifications and adaptations of the embodiments described herein will become apparent to the skilled artisan in view of this disclosure.

For example, although some embodiments measure reflectance of region 303I, other embodiments may measure other properties of region 303I, such as the temperature of region 303I by measuring measure radiation emitted by the region being evaluated.

As another example, although in some embodiments, all of light 390 (FIG. 3D) that is reflected from an illuminated region 303I is measured, in some embodiments, only via-hole component 392 included in light 390 is measured, by taking into account only light which is a certain number of degrees out of phase with the modulation of the heating beam (e.g. 180° for a substrate that uses copper as conductive layer 301). Note also that the number of degrees by which a measurement is out of phase relative to the modulation depends on several factors, such as the material used to form conductive layer 301, the material used to form dielectric layer 302, adhesion of conductive line to dielectric layer, and thermal conductivity of material of conductive lines (especially for very fine lines e.g., <100 nm in width).

As yet another example, beams 711 and 712 are concentric with one another in some embodiments as shown in FIGS. 7B and 7C, although in other embodiments these beams are only partially overlapping or in still other embodiments these beams are not overlapping at all.

Moreover, multiple regions of a wafer 300 may be simultaneously heated by a heating beam in accordance with the invention, and a camera (or an array of photodetectors in a thermal imager) may be used to perform multiple measurements simultaneously, e.g. to provide increased throughput in the evaluation of wafers during fabrication.

Although in some embodiments the heating beam and the probe beam are both focused on a single spot, in other embodiments these two beams are offset from one another to form two spots that may or may not overlap one another, depending on the embodiment. In several such embodiments, the two spots are kept sufficiently close to one another to ensure that the effect of non-thermal-wave (i.e. linear) heat transfer from the heating beam's spot is noticeable in the probe beam's spot.

Figure 11B:
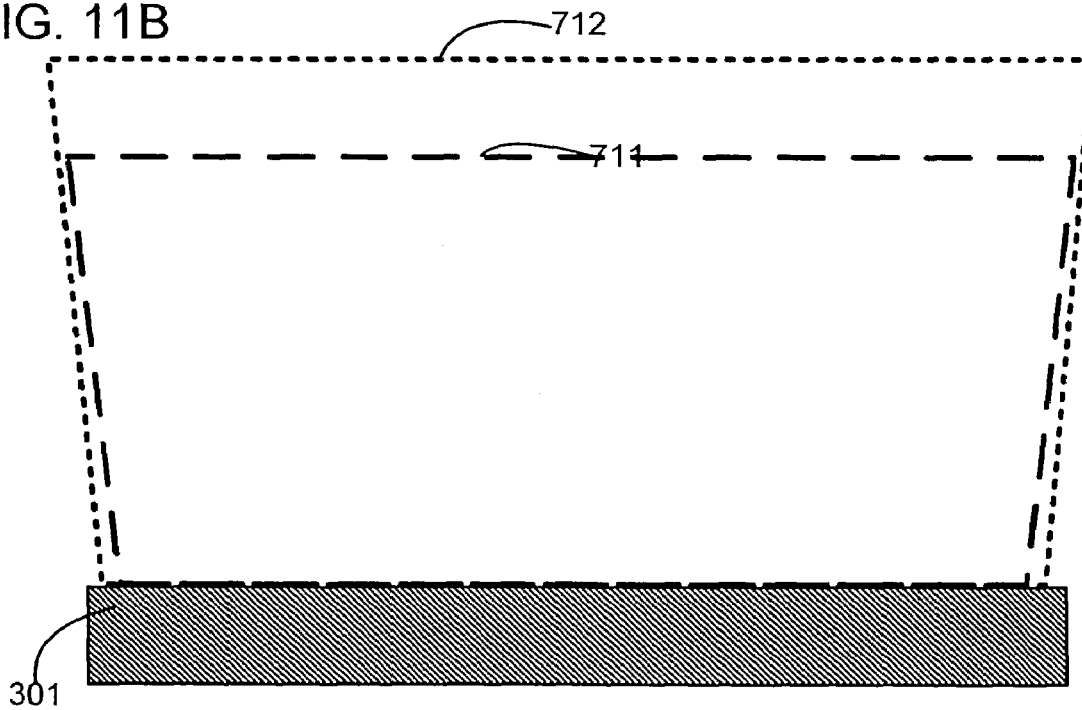
FIG. 11B illustrates, in a cross-sectional side view, use of a heating beam and a probe beam in the embodiments of FIG. 11A, to measure reflectance of a conductive layer before formation of the patterned dielectric layer.
Figure 11A:
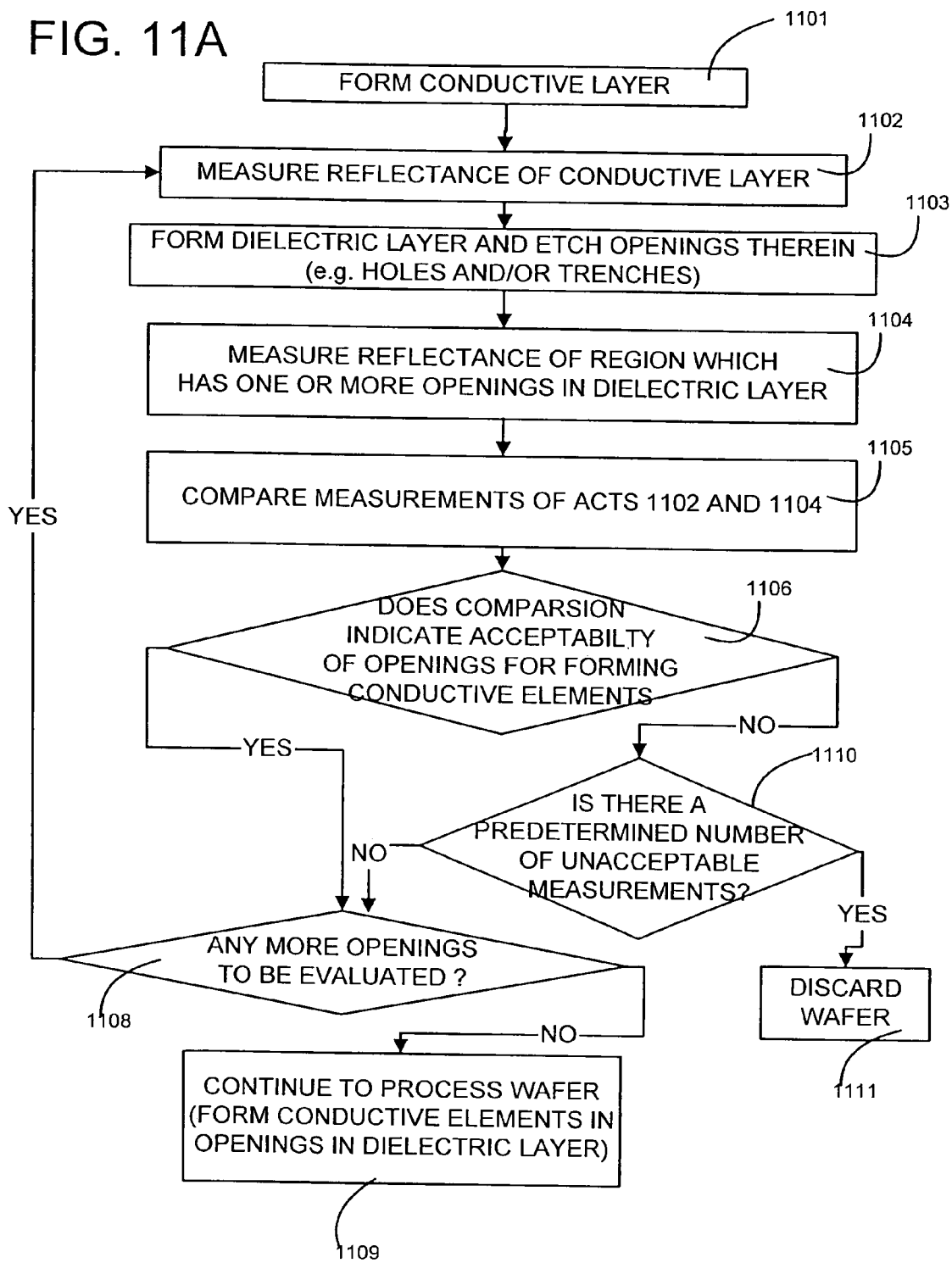
FIG. 11A illustrates, in a flow chart, acts performed in some embodiments of the invention to make reflectance measurements before and after formation of a patterned dielectric layer, followed by comparison of the measurements.

Furthermore, in some embodiments two measurements are made in an identical manner except that a first measurement is made by prior to formation of a dielectric layer over the conductive layer, while the second measurement is made subsequent to formation of the dielectric layer, and the two measurements are compared to one another to decide whether or not the wafer is to be processed further. Specifically, as illustrated in FIG. 11A, a conductive layer is formed in the normal manner as per act 1101, followed by measuring of reflectance as per act 1102. Note that the conductive layer may be patterned to form links of the type described above.

Act 1102 is performed in the manner described above in reference to FIGS. 2 and 7A in some embodiments of the invention, except that there is no dielectric layer and hence no openings therein. Act 1102 may be performed by use of a heating beam that is modulated and a probe beam whose reflectance is measured in conformity with the modulation, as illustrated in FIG. 11B, in a manner similar or identical to that described above. Note that the heating beam wavelength may be larger than the dimensions of the openings and/or links, as described above.

Next, in the embodiments illustrated in FIG. 11A, the dielectric layer is formed as per act 1103 and openings such as via holes and/or trenches are etched into the dielectric layer. After etching a clean step is performed (not shown in FIG. 11A), followed by measuring of reflectance as per act 1104 which is again performed as per FIGS. 2 and 7A. Next, as per act 1105 the two measurements from acts 1102 and 1104 are compared, e.g. by subtraction of one measurement from the other measurement in one embodiment or by division of one measurement by the other measurement in another embodiment.

The result of comparison is used, as per act 1106 to decide if the openings in the measurement region are acceptable. For example, the result of comparison is checked against a predetermined upper limit and lower limit, and if within the limits then act 1108 is performed else act 1110 is performed. In act 1108 if there are more openings to be evaluated, then control returns to act 1102, else act 1109 is performed wherein the wafer is further processed. For example, in act 1109, the openings that were etched into the dielectric layer in act 1103 are filled with conductive material to form conductive vias or conductive lines, followed by formation of the next conductive layer over the dielectric layer.

Note that comparison of measurements as described above in act 1105 is effective in indicating cleanliness of the wafer for further processing because the presence of residue significantly affects the reflectance and absorptance properties of the wafer. This method is particularly effective when using a heating beam that has a wavelength preselected to ensure that reflectance measured in act 1102 is very high (e.g. 97%) which is at least two times larger (and in many embodiments one or more orders of magnitude larger) than absorptance (e.g. 3%).

Note that there are two types of barrier layers that are used in some embodiments of the type described herein. One barrier is an etch stop layer that is embedded in the dielectric stack. This barrier can be a thin silicon nitride. Its purpose is to enable etching of the low-k material to a known depth. Another type of barrier is a thin metal film (usually TaN) that is deposited immediately before the copper seed layer, to enhance adhesion of the Cu seed and to prevent copper diffusion.

In many embodiments, each of heating beam and probe beam have sufficiently long wavelengths, so that both beams are in conformance with the above-described relationship $\omega<<\omega_p$. Other embodiments use a probe beam with a shorter wavelength. Specifically such embodiments obtain a large change in reflection with temperature based on a heating beam in conformance with relationship $\omega<<\omega_p$ while having a small probe beam spot size by virtue of the shorter wavelength probe beam. In some embodiments, a benefit of reflection vs. temperature is best obtained near the plasma frequency $\omega_p$ for both beams.

Numerous modifications and adaptations of the embodiments described herein are encompassed by the scope of the invention.

What is claimed is:

1. A method for evaluating a structure in a substrate formed by a process, said process having at least one process parameter, the method comprising:
measuring reflectance of the substrate in a region having at least one opening in a dielectric layer;
wherein said measuring is performed by use of a heating beam and a probe beam traveling through at least said dielectric layer and said at least one opening in said dielectric layer to illuminate a conductive layer underneath said dielectric layer; and
a programmed computer providing an output based at least partially on using a measurement from said measuring, said output being indicative of a change in the at least one process parameter, for use of said process in forming another structure of another substrate.

2. The method of claim 1 wherein:
said region is sufficiently large to contain a plurality of openings in addition to said at least one opening; and
light of wavelength greater than a diameter of said openings is used during measuring.

3. The method of claim 2 wherein:
a plurality of elements of conductive material are located underneath the dielectric layer; and
the plurality of elements have a length smaller than the wavelength of light used during measuring.

4. The method of claim 2 wherein:
reflectance of light from a conductive material located underneath the dielectric layer is at least an order of magnitude larger than absorptance of light by the conductive material.

5. The method of claim 1 wherein:
said region has a residue in said at least one opening; and
the measurement in said region is different from a corresponding measurement in another region that does not have residue.

6. The method of claim 1 wherein:
the measurement in said region is different from a corresponding measurement in another region that does not have residue.

7. The method of claim 1 wherein said region is hereinafter "first region", the method further comprising:
repeating said measuring in a second region that is devoid of openings; and
correcting the measurement from said first region by comparison with another measurement from said second region.

8. The method of claim 7 wherein:
said repeating is performed prior to formation of said at least one opening.

9. The method of claim 1 further comprising:
forming said at least one opening in the dielectric layer by using the at least one process parameter, prior to said measuring; and
changing the at least one process parameter depending at least partially on said output.

10. The method of claim 1 wherein:
a structure, located, underneath the dielectric layer and exposed through said at least one opening, comprises copper.

11. The method of claim 10 wherein:
said structure comprises a barrier layer.

12. The method of claim 1 further comprising:
forming a seed layer after formation of said opening and prior to said measuring.

13. The method of claim 1 further comprising:
comparing the measurement with a predetermined limit.

14. The method of claim 1 further comprising:
performing said measuring at a plurality of sites;
wherein during said using, a standard deviation is computed of said measurement and additional measurements from said performing; and
processing is discontinued on the substrate if a predetermined number of said measurements falls beyond a predetermined multiple of standard deviation.

15. The method of claim 1 further comprising:
cleaning residue from the bottom of said at least one opening in the dielectric layer prior to said measuring; and
using said measurement as an indication of cleanliness of the substrate.

16. The method of claim 1 wherein:
the change in the at least one process parameter is further used with said process in forming another opening in said another structure.

17. A method for determining a property of a substrate formed by a process, said process having at least one process parameter, the method comprising:
illuminating a region of the substrate with a heating beam and a probe beam, with power of the heating beam being modulated according to a predetermined waveform;
wherein a portion of each beam is incident on a dielectric layer in the substrate and travels through at least a part of the dielectric layer to reach a first conductive layer underneath the dielectric layer;
wherein another portion of each beam travels through at least one opening in the dielectric layer to be incident on the first conductive layer;
wherein reflectance of the heating beam by the first conductive layer is at least two times larger than absorptance of the heating beam by the first conductive layer;
measuring power of the probe beam after reflection from the first conductive layer;
wherein after reflection a component of the probe beam travels back through the part of the dielectric layer and another component of the probe beam travels through the opening;
wherein the probe beam's power that is measured is modulated at the predetermined waveform of modulation of the heating beam; and
using a measurement from said measuring, to provide a signal indicative of a change in the at least one process parameter.

18. The method of claim 17 further comprising:
repeating said illuminating in a second region that is devoid of openings so that each beam travels through the dielectric layer to reach the first conductive layer underneath the dielectric layer; and
repeating said measuring after reflection of the second beam from the first conductive layer and travel back through the dielectric layer; and
using a second measurement from said second region to correct a first measurement from said region for variation in a parameter not related to presence of vias.

19. The method of claim 17 wherein:
the first conductive layer is patterned into a plurality of elements of length smaller than a wavelength of the heating beam; and
the predetermined frequency is sufficiently small to ensure that a majority of heat that is generated by absorption of power of the heating beam in the plurality of elements transfers out of the region by diffusion through the dielectric layer but not by a thermal wave.

20. The method of claim 17 wherein:
the reflectance is at least an order of magnitude larger than the absorptance.

21. The method of claim 17 wherein:
said measuring comprises using a lock-in detector tuned to said predetermined waveform.

22. The method of claim 17 wherein the predetermined waveform in includes frequency components smaller than a maximum frequency, the maximum frequency is inversely related to at least one of:
  (a) length of a conductive line present in the region as a portion of the underlying conductive layer; and
  (b) distance at which the temperature of the conductive line is an order of magnitude smaller than the temperature in the region.

23. The method of claim 17 wherein:
said measuring comprises using a lock-in detector tuned to said predetermined waveform.

24. The method of claim 17 further comprising:
forming a seed layer on the underlying conductive layer after formation of said opening and prior to said measuring;
wherein during said illuminating, the two beams travel through the seed layer to reach the underlying conductive layer.

25. The method of claim 17 further comprising:
forming a barrier layer on the underlying conductive layer prior to said forming of seed layer;
wherein during said illuminating, at least a portion of the two beams travel through the barrier layer to reach the underlying conductive layer.

26. The method of claim 17 wherein:
the heating beam has a wavelength greater than inverse of $\omega_p$; and
$\omega_p$ is the plasma frequency of free electron gas in a conductive material in the first conductive layer in the substrate.

27. The method of claim 26 wherein:
the conductive material is copper; and
the heating beam wavelength is greater than 620 nanometers.

28. The method of claim 26 wherein:
the conductive material is aluminum; and
the heating beam wavelength is greater than 120 nanometers.

29. The method of claim 17 wherein:
the change in the at least one process parameter is for use of said process in forming another opening in another structure in another substrate.

30. A method for evaluating a substrate formed by a process, said process having at least one process parameter, the method comprising:
measuring reflectance of a conductive layer in the substrate prior to formation of a dielectric layer over the conductive layer, to obtain a first measurement;
measuring reflectance through at least one opening in the dielectric layer subsequent to formation of the dielectric layer over the conductive layer, to obtain a second measurement;
wherein said measuring to obtain said second measurement is performed by use of a heating beam and a probe beam traveling through at least a part of said dielectric layer and said at least one opening in said dielectric layer to illuminate said conductive layer underneath said dielectric layer;
comparing said first measurement and said second measurement; and
a programmed computer providing an output based on a result of said comparing;
wherein said output is indicative of a change in the at least one process parameter.

31. The method of claim 30 wherein:
said first measurement and said second measurement are made in a region sufficiently large to contain a plurality of openings in addition to said at least one opening; and
light of wavelength greater than a diameter of said openings is used during measuring.

32. The method of claim 30 wherein:
a plurality of elements of conductive material are located in the conductive layer underneath the dielectric layer; and
the plurality of elements have a length smaller than the wavelength of light used during measuring.

33. The method of claim 30 wherein:
when the first measurement is made, reflectance of light from the conductive layer is at least an order of magnitude larger than absorptance of light by the conductive layer.

34. The method of claim 30 wherein:
the change is for use of said process in forming another opening in said another structure in another substrate.

35. A method for evaluating a substrate, the method comprising:
measuring reflectance of the substrate in a first region having at least one opening in a dielectric layer;
wherein said measuring is performed by use of a heating beam and a probe beam traveling through at least a part of said dielectric layer and said at least one opening in said dielectric layer to illuminate a conductive layer underneath said dielectric layer; and
a computer providing an output to a human operator, based at least partially on a measurement from said measuring.

36. The method of claim 35 wherein:
said region is sufficiently large to contain a plurality of openings in addition to said at least one opening; and
light of wavelength greater than a diameter of said openings is used during measuring.

37. The method of claim 35 wherein said region is hereinafter "first region", the method further comprising:
repeating said measuring in a second region that is devoid of openings; and
correcting the measurement from said first region by comparison with another measurement from said second region.

38. The method of claim 35 further comprising:
forming said at least one opening in the dielectric layer by using the at least one process parameter, prior to said measuring; and
changing the at least one process parameter depending at least partially on said output.

39. The method of claim 35 further comprising:
comparing the measurement with a predetermined limit.

40. The method of claim 35 further comprising:
cleaning residue from the bottom of said at least one opening in the dielectric layer prior to said measuring; and
using said measurement as an indication of cleanliness of the substrate.

41. The apparatus of claim 35 wherein:
power of the heating beam is modulated according to a predetermined waveform.

42. The method of claim 35 wherein:

the heating beam has a wavelength greater than inverse of $\omega p$; and $\omega p$ is the plasma frequency of free electron gas in a conductive material in the conductive layer.

43. The method of claim 35 wherein:

a plurality of elements of conductive material are located in the conductive layer underneath the dielectric layer; and the plurality of elements have a length smaller than the wavelength of light used during said measuring.

44. An apparatus for evaluating a substrate, the apparatus comprising:

a first source of a heating beam;

a second source of a probe beam; and a photodetector to sense intensity of a portion of said probe beam reflected from the substrate, in a region of the substrate having at least one opening in a dielectric layer;

wherein said heating beam and said probe beam travel through at least a part of said dielectric layer and through said at least one opening in said dielectric layer to illuminate a conductive layer underneath said dielectric layer.

45. The apparatus of claim 44 further comprising:

a programmed computer coupled to the photodetector;

wherein the programmed computer provides an output to a human operator.

46. The apparatus of claim 44 further comprising:

a programmed computer coupled to the photodetector;

wherein the programmed computer provides an output based at least partially on detecting a defect in said dielectric layer.

47. The apparatus of claim 44 wherein:

power of the heating beam is modulated according to a predetermined waveform; and the apparatus further comprises a lock-in detector tuned to said predetermined waveform.

48. The apparatus of claim 44 wherein:

the heating beam has a wavelength greater than inverse of $\omega_p$; and $\omega_p$ is the plasma frequency of free electron gas in a conductive material in the conductive layer in the substrate.

* * * * *